US008049067B2

(12) United States Patent
Firoozabady

(10) Patent No.: US 8,049,067 B2
(45) Date of Patent: *Nov. 1, 2011

(54) ORGANOGENIC TRANSFORMATION AND REGENERATION

(75) Inventor: Ebrahim Firoozabady, Pleasant Hill, CA (US)

(73) Assignee: Del Monte Fresh Produce Company, Coral Gables, FL (US)

( * ) Notice: Subject to any disclaimer, the term of this patent is extended or adjusted under 35 U.S.C. 154(b) by 448 days.

This patent is subject to a terminal disclaimer.

(21) Appl. No.: 10/536,885

(22) PCT Filed: Dec. 8, 2003

(86) PCT No.: PCT/US03/38912
§ 371 (c)(1),
(2), (4) Date: May 31, 2005

(87) PCT Pub. No.: WO2004/053082
PCT Pub. Date: Jun. 24, 2004

(65) Prior Publication Data
US 2006/0130171 A1    Jun. 15, 2006

Related U.S. Application Data

(60) Provisional application No. 60/431,323, filed on Dec. 6, 2002.

(51) Int. Cl.
*C12N 15/52* (2006.01)
*C12N 15/82* (2006.01)
(52) U.S. Cl. ......... 800/294; 800/282; 800/288; 800/298
(58) Field of Classification Search .................. None
See application file for complete search history.

(56) References Cited

U.S. PATENT DOCUMENTS

| | | |
|---|---|---|
| 4,945,050 A | 7/1990 | Sanford et al. |
| 5,262,316 A | 11/1993 | Engler et al. |
| 5,429,939 A | 7/1995 | Misawa et al. |
| 5,530,188 A | 6/1996 | Ausich et al. |
| 5,530,189 A | 6/1996 | Ausich et al. |
| 5,589,581 A | 12/1996 | Misawa et al. |
| 5,591,616 A | 1/1997 | Hiei et al. |
| 5,618,988 A | 4/1997 | Hauptmann et al. |
| 5,656,472 A | 8/1997 | Ausich et al. |
| 5,684,238 A | 11/1997 | Ausich et al. |
| 5,744,341 A | 4/1998 | Cunningham, Jr. et al. |
| 5,750,865 A | 5/1998 | Bird et al. |
| 5,792,903 A | 8/1998 | Hirschberg et al. |
| 5,908,771 A | 6/1999 | Liu et al. |
| 5,952,543 A * | 9/1999 | Firoozabady et al. ........ 800/294 |
| 5,955,269 A | 9/1999 | Ghai et al. |
| 6,037,522 A | 3/2000 | Dong et al. |
| 6,087,563 A | 7/2000 | DellaPenna et al. |
| 6,133,035 A | 10/2000 | Engler et al. |
| 6,140,553 A | 10/2000 | D'Halluin |
| 6,140,555 A | 10/2000 | Reichert et al. |
| 6,194,639 B1 | 2/2001 | Botella et al. |
| 6,214,575 B1 | 4/2001 | Yano et al. |
| 6,239,331 B1 | 5/2001 | Drake et al. |
| 6,242,257 B1 | 6/2001 | Tuli et al. |
| 6,252,141 B1 | 6/2001 | Hirschberg et al. |
| PP12,861 P2 | 8/2002 | Loison |
| 6,429,356 B1 | 8/2002 | Shewmaker |
| 6,653,530 B1 * | 11/2003 | Shewmaker et al. ......... 800/282 |
| 2002/0092039 A1 | 7/2002 | Shewmaker |
| 2002/0102631 A1 | 8/2002 | Cunningham, Jr. et al. |
| 2002/0142281 A1 | 10/2002 | Broun |
| 2006/0130171 A1 | 6/2006 | Firoozabady |

FOREIGN PATENT DOCUMENTS

| | | |
|---|---|---|
| EP | 604662 A1 | 7/1994 |
| EP | 672752 A1 | 9/1995 |
| WO | WO 88/02405 A1 | 4/1988 |
| WO | WO 95/06741 | 3/1995 |
| WO | WO 96/13149 | 5/1996 |
| WO | WO 98/36637 A1 | 8/1998 |
| WO | WO 98/37212 A1 | 8/1998 |
| WO | WO 99/15003 | 4/1999 |
| WO | WO 99/19499 | 4/1999 |
| WO | WO 99/58644 | 11/1999 |
| WO | WO 99/58644 A1 | 11/1999 |
| WO | WO 00/15813 | 3/2000 |
| WO | WO 01/12828 A1 | 2/2001 |
| WO | WO 01/33943 | 5/2001 |
| WO | WO 01/33943 A1 | 5/2001 |
| WO | WO 01/73084 A2 | 10/2001 |
| WO | WO 01/94602 | 12/2001 |
| WO | WO 02/14523 | 2/2002 |
| WO | WO 02/37951 A1 | 5/2002 |
| WO | WO 02/052025 A2 | 7/2002 |
| WO | WO 02/057464 A2 | 7/2002 |
| WO | WO 2004/052085 | 6/2004 |

OTHER PUBLICATIONS

Mezzetti B. et al. BMC Biotechnology; vol. 2, No. 18 published Sep. 27, 2002.*
Sripaoraya S. et al. Annals of Botany (Oct. 2001) 88: pp. 597-603.*
Firoozabady E et al. (1995) "In vitro plant regeneration and advanced micropropagation methods for pineapple" vol. 31, p. 51.
Frulleux et al. (1997) "*Agrobacterium tumefaciens*-mediated transformation of shoot-buds of chicory" Plant Cell Tissue and Organ Culture, vol. 50, No. 2 pp. 107-112.
Kiss, E et al. (1995) "A novel method for rapid micropropagation of pineapple" Hortscience, vol. 30, No. 1, pp. 127-129.
Mezzetti Bruno et al. (Sep. 27, 2002) "Genetic transformation of *Vitis vinifera* via organogenesis" BMC Biotechnology, vol. 2, No. 18.
Sripaoraya et al. (2001) "Herbicide-tolerant transgenic pineapple (*Ananas comosus*) produced by microprojectile bombardment" Annals of Botany, vol. 88, No. 4, pp. 597-603.
Xie and Hong (Mar. 2002) "*Agrobacterium*-mediated genetic transformation of *Acacia mangium*" Plant Cell Reports vol. 20, No. 10, pp. 917-922.
Bordoloi and Sarma (1993) "In vitro callus induction and plantlet regeneration of pineapple," *J Assam Science Society* 35(1):41-45.

(Continued)

*Primary Examiner* — Russell Kallis
(74) *Attorney, Agent, or Firm* — Quine Intellectual Property Law Group, P.C.; Jonathan Alan Quine

(57) ABSTRACT

This invention provides methods of transforming organogenic plant cells and regenerating plants from transformed cells.

7 Claims, No Drawings

OTHER PUBLICATIONS

Caboche and Deshayes. (1984) "Biologie moleculaire—utilisation de liposomes pour la transformation de porotoplastes de mesoplylle de tabac par un plasmide recombinant de *E coli* leur conferant la resistance a la kanamycine," *Comptes Rendus Acad. Sci.* 299, series 3:66.

Callis et al. (1987). "Introns increase gene expression in cultured maize cells," *Genes and Development*, 1:1183-1200.

Crossway et al. (1986). "Integration of foreign DNA following microinjection of tobacco mesophyll protoplasts," *Mol. Gen. Genet.*, 202:179-185.

Crossway et al. (1986). "Micromanipulation Techniques in Plant Biotechnology," *BioTechniques* 4(4):320-334.

De La Pena et al. (1987) "Transgenic rye plants obtained by injecting DNA into young floral tillers," *Nature*, 325:274-276.

De Wet et al. (1985) "Exogenuous gene transfer in maize (*Zea mays*) using DNA-treated pollen," *The Experimental Manipulation of Ovule Tissues*, Chapman et al. (Eds.), Longman, p. 197-209.

Dewald et al. (1988) "Production of pineapple plants in vitro," *Plant Cell Reports*, 7:535-537.

Fennell and Hauptmann. (1992) "Electroporation and PEG delivery of DNA into maize microspores," *Plant Cell Reports*, 11:567-570.

Firoozabady and Moy (2004) "Regeneration of pineapple plants via somatic embryogenesis and organogenesis," In Vitro *Cellular and Developmental Biology—Plant*, 40(1): 67-74.

Fitchet (1990) "Organogenesis in Callus Cultures of Pineapple," *Acta Hort*, 275:267-274.

Fraley et al. (1983) "Expression of bacterial genes in plant cells." *Proceeding of the National Academy of Sciences, USA*, 80: 4803-4807.

Fraley et al. (1985) "The Sev System: A New Disarmed TI Plasmid Vector System for Plant Transformation," *Bio/technology*, 3:629-635.

Frame et al. (1994) "Production of fertile transgenic maize plants by silicon carbide whisker-mediated transformation," *The Plant Journal* 6:941-948.

Fromm et al. (1986) "Stable transformation of maize after gene transfer by electroporation." *Nature*, 319:791-793.

Gamborg (1984) "Plant Cell Cultures: Nutrition and Media," Ed. Indra K. Vasil, *Cell Culture and Somatic Cell Genetics of Plants*, 1:18-26.

Hinchee et al. (1988) "Production of Transgenic Soybean Plants Using *Agrobacterium*-Mediated DNA Transfer," *Bio/technology*, 6:915-922.

Horsch et al. (1985) "A simple and general method of transferring genes into plants," *Science*, 227:1229-1231.

Jorgensen et al. (1987) "T-DNA is organized predominantly in inverted repeat structures in plants transformed with *Agrobacterium tumefaciens* C58 derivatives," *Mol. Gen. Genet.*, 207:471-477.

Klein et al. (1987) "High-velocity microprojectiles for delivering nucleic acids into living cells," *Nature*, 327:773.

Klein et al. (1988) "Stable genetic transformation of intact *Nicotiana* cells by the particle bombardment process." *Proceeding of the National Academy of Sciences, USA*, 85: 8502-8505.

Lorz et al. (1985) "Gene transfer to cereal cells meditated by protoplast transformation," *Mol. Gen. Genet.*, 199:178-182.

Luo and Wu (1988) "A simple method for the transformation of rice via the pollen-tube pathway," *Plant Mol. Biol. Reporter*, 6(3):165-174.

Luo and Wu. (1989) "A simple method for the transformation of rice via the pollen-tube pathway," *Plant Mol. Biol. Rep.* 7(1):69-77.

Marcotte et al. (1988) "Regulation of a wheat promoter by abscisic acid in rice protoplasts," *Nature*, 335:454-457.

Mathews and Rangan (1981) "Growth and regeneration of plantlets in callus cultures of pineapple," *Scientia Hort* 14:227-234.

McCabe et al. (1988) "Stable transformation of soybean (glycine max) by particle acceleration," *Biotechnology*, 6:923-926.

Paszkowski et al. (1989) "Direct gene transfer to plants." *EMBO J.* 3(12):2717-2722.

Potrykus et al. (1985) "Direct gene transfer to cells of a *Graminaceous monocot*." *Mol. Gen. Genet.*, 199:183-188.

Rangan (1984) "Pineapple," *Handbook of Plant Cell Culture*, Eds. P.K. Ammirato et al. New York: MacMillan Pub. Co., 3:373-382.

Reich et al. (1986) "Efficient transformation of alfalfa protoplasts by the intranuclear microinjection of Ti plasmids," *Bio/technology*,4:1001-1004.

Riggs and Bates (1986) "Stable transformation of tobacco by electroporation: Evidence for plasmid concatenation." *Proceeding of the National Academy of Sciences, USA*, 83: 5602-5606.

Rogers and Klee. (1985) "Pathways to plant genetic manipulation employing *Agrobacterium*," *Plant DNA Infectious Agents*, Eds. Hohn and Schell, Springer-Verlag pp. 179-203.

Rogers et al. (1987) "Improved vectors for plant transformation: expression cassette vectors and new selectable markers," *Methods in Enzymology*, 153:253-277.

Schardl et al. (1987) "Design and construction of a versatile system for the expression of foreign genes in plants," *Gene* 61:1-11.

Spielmann and Simpson. (1986) "T-DNA structure in transgenic tobacco plants with multiple independent integration sites," *Mol. Gen. Genet.*, 205:34-41.

Srinivasa et al. (1981) "Differentiation of plantlets in hybrid embryo callus of pineapple," *Scientia Hort* 15: 235-238.

Staub and Maliga. (1993) "Acculmulation of D1 polypeptide in tobacco plastids is regulated via the untranslated region of the *psbA* mRNA," *Embo J.* 12(2):601-606.

Svab et al. (1990) "Stable transformation of plastids in higher plants." *Proceeding of the National Academy of Sciences, USA*, 87: 8526-8530.

Svab et al. (1993) "High-frequency plastid transformation in tobacco by selection for a chineric aadA gene." *Proceeding of the National Academy of Sciences, USA*, 90: 913-917.

Uchimiya et al. (1986) "Expression of a foreign gene in callus derived from DNA-treated protoplasts of rice (*Oryza sativa* L.,)" *Mol. Gen. Genet.*, 204:204-207.

Vasil et al. (1992) "Herbicide resistant fertile transgenic wheat plants obtained by microprojectile bombardment of regenerable embryogenic callus," *Bio/Technology*, 10:667-674.

Wakasa et al. (1978) "Differentiation from in sitro culture of *Ananas comosus*," *Japan J Breed*, 28(2):113-121.

Wang et al. (1992) "Transgenic plants of tall fescue (*Festuca arundinacea* Schreb.) obtained by direct gene transfer to protoplasts," *Bio/Technology*, 10:691-696.

Weber (1988) "Microperforation of plant tissue with a UV laser microbeam and injection of DNA into cells," *Naturwissenschaften* 75:35-36.

Hajdukiewicz et al. (2001) "Multiple pathways for Cre/lox-mediated recombination in plastids," *The Plant Journal*, 27(2):161-170.

Hirschberg (2001) "Carotenoid biosynthesis in flowering plants," *Current Opinion in Plant Biology*, 4:210-218.

Israeli office action, dated Feb. 11, 2009 cited in IL 168921 (Israeli counterpart of U.S. Appl. No. 10/536,885).

Dewald, M. et al. (1988) "Production on pineapples plants in vitro" Plant Cell Report, vol. 7, No. 7, pp. 535-537.

\* cited by examiner

ORGANOGENIC TRANSFORMATION AND REGENERATION

CROSS-REFERENCE TO RELATED APPLICATIONS

This application is the national phase under 35 U.S.C. §371 of International Application No. PCT/US2003/038912, which has an International filing date of Dec. 8, 2003 and which designated the United States of America, which is a continuation-in-part of International Application No. PCT/US2003/038664, filed Dec. 5, 2003, which claims the benefit of U.S. Provisional Application No. 60/431,323, filed Dec. 6, 2002, which are each incorporated by reference in their entirety for all purposes.

FIELD OF THE INVENTION

The present invention relates generally to plant biotechnology, providing methods of transforming and regenerating plants.

BACKGROUND OF THE INVENTION

It has become possible to transfer nucleic acids from a wide variety of organisms to plants utilizing recombinant DNA technology. For example, this technology has provided a mechanism to improve various agronomic properties including plant resistance to drought, temperature extremes, pests, diseases, and herbicides. However, the lack of efficient and reproducible transformation and regeneration from plant cell culture systems for many agriculturally significant crops has been a substantial barrier to the application of genetic engineering technology to plants. Moreover, there is a potential for the occurrence of somaclonal variation when plants are regenerated adventitiously in vitro. Somaclonal variation is genetic variability commonly observed in plants that originate from, e.g., a callus intermediate. This genetic variability is typically undesirable as the maintenance of the genetic integrity of transformed plants is generally an objective.

SUMMARY OF THE INVENTION

The present invention provides methods for the transformation of organogenic plant cells and for the regeneration of plants directly from transformed organogenic cells. The methods described herein are generally more efficient than many pre-existing plant transformation and regeneration methodologies. In addition, the methods of the present invention typically minimize the potential for the occurrence of somaclonal variation, as plants are regenerated from organogenic cells or tissues rather than from calli or embryogenic cells. Nucleic acids are introduced into cells using essentially any delivery technique, including *Agrobacterium*-mediated delivery, and can confer a wide range of desired agronomic properties. These and a variety of other features of the present invention will be apparent upon a complete review of the following disclosure.

In one aspect, the invention provides a method of producing transformed plant cells. The method includes culturing at least one non-apical meristemic cell to produce one or more organogenic cells, and introducing at least one nucleic acid segment into the organogenic cells to produce one or more transformed organogenic cells. In certain embodiments, the method further includes generating at least one plant from the transformed organogenic cells.

In another aspect, the invention relates to a method of producing transformed plant cells that includes culturing at least one meristemic cell to produce at least one shoot. In addition, the method also includes culturing at least one explant from the shoot to produce one or more organogenic cells. In certain embodiments, the explant comprises one or more non-apical meristemic cells. The method also includes introducing at least one nucleic acid segment into the organogenic cells to produce one or more transformed organogenic cells. In some embodiments, the method further includes generating at least one plant from the transformed organogenic cells.

The meristemic cells (e.g., non-apical meristemic cells) utilized in the methods of the invention are optionally derived from various sources. In some embodiments, for example, meristemic cells are derived from monocotyledonous plants, whereas in other embodiments, meristemic cells are derived from dicotyledonous plants. To further illustrate, meristemic cells utilized in the methods described herein are optionally derived from plants selected from the genera: *Ananas, Musa, Vitis, Fragaria, Lotus, Medicago, Onobrychis, Trifolium, Trigonella, Vigna, Citrus, Carica, Persea, Prunus, Syragrus, Theobroma, Coffea, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Mangifera, Cichorium, Helianthus, Lactuca, Bromus, Asparagys, Antirrhinum, Heterocallis, Nemesia, Pelargonium, Panicum, Pennisetum, Ranunculus, Senecio, Salpiglossis, Cucurbita, Cucuinis, Browaalia, Lolium, Malus, Apium, Gossypium, Vicia, Lathyrus, Lupinus, Pachyrhizus, Wisteria, Stizolobium, Agrostis, Phleum, Dactylis, Sorgum, Setaria, Zea, Oryza, Triticum, Secale, Avena, Hordeum, Saccharum, Poa, Festuca, Stenotaphrum, Cynodon, Coix, Olyreae, Phareae, Glycine, Pisuin, Psidium, Passiflora, Cicer, Phaseolus, Lens, Arachis*, or the like. In certain embodiments, meristemic cells comprise pineapple cells selected from, e.g., Smooth Cayenne cells, Red Spanish cells, Perolera cells, Pernambuco cells, Primavera cells, or the like.

Nucleic acid segments introduced into organogenic cells according to the methods of the present invention typically confer one or more desired agronomic properties on the transformed cells and/or plants generated therefrom. In some embodiments, for example, nucleic acid segments confer resistance to the transformed organogenic cells from insects, drought, nematodes, viral disease, bacterial disease, herbicides, and/or the like. In certain embodiments, nucleic acid segments encode polypeptides (e.g., plant polypeptides, bacterial polypeptides, etc.). Optionally, the polypeptide is artificially evolved. In certain embodiments, polypeptides are heterologous to the organogenic cells. In some embodiments, polypeptides are homologous to at least one endogenous polypeptide of the organogenic cells. To illustrate, nucleic acid segments optionally comprise or encode, e.g., ACC synthases, ACC oxidases, malic enzymes, malic dehydrogenases, glucose oxidases, chitinases, defensins, expansins, hemicellulases, xyloglucan transglycosylases, apetala genes, leafy genes, knotted-related genes, homeobox genes, Etr-related genes, ribonucleases, and/or the like. To illustrate further, polypeptides optionally comprise at least one carotenoid biosynthetic polypeptide that is selected from, e.g., an isopentenyl diphosphate isomerase, a geranylgeranyl pyrophosphate synthase, a phytoene synthase, a phytoene desaturase, a ζ-carotene desaturase, a lycopene β-cyclase, a lycopene ε-cyclase, a β-carotene hydroxylase, an β-hydroxylase, and/or the like.

In some embodiments, nucleic acid segments stably integrate into the genome of the transformed organogenic cells, whereas in other embodiments, nucleic acid segments are only transiently present in organogenic cells. Nucleic acid segments optionally include selectable markers, e.g., such that the introduction of the segments into cells can be confirmed. In certain embodiments, nucleic acid segments are operably linked to a constitutive promoter. In other embodiments, nucleic acid segments are operably linked to an inducible promoter. In some embodiments, nucleic acid segments encode at least one polypeptide transcription factor. In certain embodiments, nucleic acid segments encode at least one promoter and/or at least one enhancer, which nucleic acid segments homologously recombine with at least one promoter and/or at least one enhancer of at least one endogenous gene. In some embodiments, nucleic acid segments comprise sense nucleic acid segments that correspond to at least a portion of at least one endogenous gene. In other embodiments, nucleic acid segments comprise at least one sense nucleic acid segment that corresponds to at least a portion of at least one exogenous gene. Optionally, nucleic acid segments comprise at least one antisense nucleic acid segment that corresponds to at least a portion of at least one endogenous gene.

Nucleic acids can be introduced into cells according to the methods of the invention using essentially any technique. In some embodiments, for example, nucleic acid segments are introduced into the organogenic cells using *Agrobacterium*-mediated delivery. To further illustrate, nucleic acid segments are optionally introduced into the organogenic cells using at least one nucleic acid delivery technique selected from, e.g., pollen-mediated delivery, direct nucleic acid transfer to at least one protoplast of the organogenic cells, microprojectile bombardment, microinjection, macroinjection of inflorescence, whisker-mediated impregnation, laser perforation, ultrasonification, and/or the like.

DETAILED DESCRIPTION

I. Definitions

Before describing the present invention in detail, it is to be understood that this invention is not limited to particular embodiments. It is also to be understood that the terminology used herein is for the purpose of describing particular embodiments only, and is not intended to be limiting. Units, prefixes, and symbols are denoted in the forms suggested by the International System of Units (SI), unless specified otherwise. Numeric ranges are inclusive of the numbers defining the range. As used in this specification and the appended claims, the singular forms "a", "an" and "the" also include plural referents unless the context clearly dictates otherwise. Thus, for example, reference to "a cell" also includes two or more cells (e.g., in the form of a tissue, etc.), and the like. Further, unless defined otherwise, all technical and scientific terms used herein have the same meaning as commonly understood by one of ordinary skill in the art to which the invention pertains. The terms defined below, and grammatical variants thereof, are more fully defined by reference to the specification in its entirety.

The term "nucleic acid" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA in solution, such as 2'-O-methylated oligonucleotides), and/or the like. A nucleic acid can be e.g., single-stranded or double-stranded. Unless otherwise indicated, a particular nucleic acid sequence of this invention encompasses complementary sequences, in addition to the sequence explicitly indicated. The term nucleic acid is used interchangeably with, e.g., oligonucleotide, polynucleotide, gene, cDNA, RNAi, and mRNA encoded by a gene.

A "nucleic acid sequence" refers to the order and identity of the nucleotides in a nucleic acid segment.

A "polynucleotide" is a polymer of nucleotides (A, C, T, U, G, etc. or naturally occurring or artificial nucleotide analogues) or a character string representing a polymer of nucleotides, depending on context. Either the given nucleic acid or the complementary nucleic acid can be determined from any specified polynucleotide sequence.

Two nucleic acids "correspond" when they have the same sequence, or when one nucleic acid is complementary to the other, or when one nucleic acid is a subsequence of the other, or when one sequence is derived, by natural or artificial manipulation from the other.

The term "gene" is used broadly to refer to any segment of a nucleic acid associated with a biological function. Thus, genes include coding sequences and optionally, the regulatory sequences required for their expression. Genes also optionally include nonexpressed DNA or RNA segments that, for example, form recognition sequences for other proteins. Genes can be obtained from a variety of sources, including cloning from a source of interest or synthesizing from known or predicted sequence information, and may include sequences designed to have desired parameters.

The term "nucleic acid segment" refers to a polynucleotide or transcribable analog thereof, of at least 25 nucleotides in length, usually at least 100 nucleotides in length, generally at least 200 nucleotides in length, typically at least 300 nucleotides in length, more typically at least 400 nucleotides in length, and most typically at least 500 nucleotides in length. To illustrate, a nucleic acid segment can include a full-length gene (e.g., a gene that encodes a polypeptide, such as a carotenoid biosynthetic polypeptide or the like), or a subsequence of such a gene.

The term "T-DNA" refers to a nucleic acid segment that can be mobilized and transferred from an *Agrobacterium* into a plant cell to thereby introduce the nucleic acid segment into the plant cell.

The term "linked" generally refers to nucleic acid segments that are contiguous with one another and, where necessary to join two amino acid coding regions, contiguous and in the same reading frame. The term "linked" also encompasses nucleic acids that co-segregate with one another. Further, the term "operably linked" or "operatively linked" refers to a functional linkage between two or more nucleic acid segments. For example, a promoter and a nucleic acid segment that encodes a polypeptide are operably linked when the promoter sequence initiates and mediates transcription of the nucleic acid segment.

The term "expression" refers to the transcription and accumulation of sense (mRNA) or antisense RNA derived from the nucleic acid segments of the invention. Expression may also refer to translation of mRNA into a polypeptide, e.g., a carotenoid biosynthetic polypeptide or the like. In certain embodiments of the invention, for example, carotenoid biosynthetic polypeptides are expressed in preselected plant storage organs, such as roots, seeds, fruits, etc., leading to enhanced accumulation of one or more carotenoids (e.g., naturally produced carotenoids) in that plant storage organ. Accordingly, the term "fruit-specific expression" refers to the expression of, e.g., introduced carotenoid biosynthetic polypeptides that is substantially limited to fruit tissues of the plants of the invention, e.g., so as to effect an altered accumulation of carotenoid that is "substantially specific to fruit tissues" of the transformed plants.

The term "promoter" refers to a recognition site on a DNA sequence or group of DNA sequences that provides an expression control element for a gene and to which RNA polymerase specifically binds and initiates RNA synthesis (transcription) of that gene. The term "constitutive promoter" refers to an unregulated promoter that allows for continual transcription of an associated gene. The term "inducible promoter" refers to a regulated promoter that allows for transcription of an associated gene in the presence of another substance or inducer, such as an extracellular molecule (e.g., a substrate of an enzyme that is encoded by the gene).

The term "selectable marker" includes reference to a gene whose expression allows one to identify cells that comprise the marker gene, such as a nucleic acid segment (e.g., a T-DNA) that includes the marker gene in addition to an encoded polypeptide. To illustrate, a selectable marker gene product may confer herbicide resistance on transformed cells such that upon exposing a population of cells to an effective amount of the herbicide, only those cells that have been transformed remain viable.

The term "sense nucleic acid segment" generally refers to a coding nucleic acid segment. In contrast, the term "antisense nucleic acid segment" typically refers a complement of a sense nucleic acid segment.

The term "transcription factor" refers to any factor that controls the process of transcription (i.e., the making of an RNA copy of a DNA segment). Usually it is an enzyme or other protein, a coenzyme, a vitamin, or another organic molecule.

The term "enhancer" refers to a DNA sequence that positively influences the expression of a gene, even if the enhancer is positioned some distance from that gene.

Two nucleic acids are "recombined" when sequences from each of the two nucleic acids are combined in a progeny nucleic acid.

A nucleic acid segment "stably integrates" into the genome of a plant or plant cell when it is non-transiently introduced into that genome. For example, a heterologous nucleic acid segment that is permanently incorporated into a plant chromosome is stably integrated into the genome of the corresponding plant cell or plant.

The term "transformation" refers to the transfer or introduction of a nucleic acid segment into a plant or plant cell, whether the introduction results in genetically stable inheritance of the nucleic acid segment or only a transient presence of the nucleic acid segment in the genome of the plant or plant cell. Plant cells or plants that include the introduced nucleic acid segments are referred to as "transgenic," "recombinant," or "transformed" plant cells or plants.

A polynucleotide sequence, such as a nucleic acid segment, is "heterologous" to an organism, or a second polynucleotide sequence, if it originates from another species, or, if from the same species, is modified from its original or native form. For example, a promoter operably linked to a heterologous coding sequence refers to a coding sequence from a species different from that from which the promoter was derived, or, if from the same species, a coding sequence which is different from a naturally occurring allelic variants.

Nucleic acids are "homologous" when they are derived, naturally or artificially, from a common ancestral sequence. Homology is often inferred from sequence similarity between two or more nucleic acids. This occurs naturally as two or more descendent sequences deviate from a common ancestral sequence over time as the result of mutation and natural selection. Artificially homologous sequences may be generated in various ways. For example, a nucleic acid sequence can be synthesized de novo to yield a nucleic acid that differs in sequence from a selected parental nucleic acid sequence. Artificial homology can also be created by artificially recombining one nucleic acid sequence with another, as occurs, e.g., during cloning or chemical mutagenesis, to produce a homologous descendent nucleic acid. Artificial homology may also be created using the redundancy of the genetic code to synthetically adjust some or all of the coding sequences between otherwise dissimilar nucleic acids in such a way as to increase the frequency and length of highly similar stretches of nucleic acids while minimizing resulting changes in amino acid sequences to the encoded gene products. Preferably, such artificial homology is directed to increasing the frequency of identical stretches of sequence of at least three base pairs in length. More preferably, it is directed to increasing the frequency of identical stretches of sequence of at least four base pairs in length. It is generally assumed that two nucleic acids have common ancestry when they demonstrate sequence similarity. However, the exact level of sequence similarity necessary to establish homology varies in the art. In general, for purposes of this disclosure, two nucleic acid sequences are deemed to be homologous when they share enough sequence identity to permit direct recombination to occur between the two sequences, that is, anywhere along the two sequences.

The term "encoding" refers to a polynucleotide sequence encoding one or more amino acids. The term does not require a start or stop codon. An amino acid sequence can be encoded in any reading frame provided by a polynucleotide sequence.

The term "vector" refers to an extra-chromosomal element that is capable of replication in a cell and/or to which other nucleic acid segments can be operatively linked so as to bring about replication of those segments. Such elements may be autonomously replicating sequences, genome integrating sequences, phage or nucleotide sequences, linear or circular, of single- or double-stranded DNA or RNA, derived from any source, in which a number of nucleotide sequences have been joined or recombined into a construct that is capable of introducing nucleic acid segments (e.g., that include one or more promoters and one or more genes that encode enzymes, etc.) along with appropriate 3' untranslated sequences into a cell. A plasmid is an exemplary vector. Vectors or vector systems (e.g., binary vectors systems, trinary vector systems, or the like) can include elements in addition to, e.g., a gene that encodes a carotenoid biosynthetic enzyme, such as those which facilitate transformation of a pineapple cell or plant, those that allow for enhanced expression of included genes (e.g., promoters) in transformed plants or plant cells, those that facilitate selection of transformed plants or plant cells (e.g., selectable markers, reporter genes, etc.), or the like. The term "expression vector" refers to an extra-chromosomal element that is capable of regulating the expression of a gene (e.g., a gene encoding a polypeptide) when operatively linked to the gene within the vector.

The term "polypeptide" refers to a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

The term "carotenoid biosynthetic polypeptide" refers to a biocatalyst or enzyme that catalyzes at least one step in the carotenoid biosynthetic pathway. Carotenoid biosynthetic polypeptides include, e.g., geranylgeranyl pyrophosphate synthases, isopentenyl diphosphate isomerases, phytoene synthases, phytoene desaturases, ζ-carotene desaturases, lycopene β-cyclases, lycopene ε-cyclases, β-carotene hydroxylases, ε-hydroxylases, and the like.

A "polypeptide sequence" refers to the order and identity of the amino acids in a polypeptide.

The term "artificially evolved polypeptide" refers to a polypeptide created using one or more diversity generating techniques. For example, artificially evolved polypeptides employed in the practice of the present invention are optionally produced by recombining (e.g., via recursive recombination or the like) two or more nucleic acids encoding one or more parental polypeptides, or by mutating one or more nucleic acids that encode polypeptides (e.g., using site directed mutagenesis, cassette mutagenesis, random mutagenesis, recursive ensemble mutagenesis, or the like). A nucleic acid encoding a parental polypeptide includes a polynucleotide or gene that, through the mechanisms of transcription and translation, produces an amino acid sequence corresponding to a parental polypeptide, e.g., an non-artificially evolved or naturally-occurring polypeptide. The term, "artificially evolved polypeptide" also embraces chimeric polypeptides that include identifiable component sequences (e.g., functional domains, etc.) derived from two or more parents. For example, artificially evolved enzymes employed in the practice of the present invention are typically evolved, e.g., to yield products with greater efficiency than naturally-occurring enzymes.

The term "endogenous" refers to a substance that is natively produced or synthesized within an organism or system.

The term "exogenous" refers to materials originating from outside of the organism or cell. It refers to nucleic acid molecules used in producing transformed or transgenic host cells and plants. As used herein, exogenous is intended to refer to any nucleic acid that is introduced into a recipient cell, regardless of whether a similar nucleic acid may already be present in such cell.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using a sequence comparison algorithms or by visual inspection.

A region of "high sequence similarity" refers to a region that is 90% or more identical to a second selected region when aligned for maximal correspondence (e.g., manually or, e.g., using the common program BLAST set to default parameters). A region of "low sequence similarity" is 30% or less identical, more preferably, 40% or less identical to a second selected region, when aligned for maximal correspondence (e.g., manually or using BLAST set with default parameters).

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using, e.g., a sequence comparison algorithm or by visual inspection. Preferably, the substantial identity exists over a region of the sequences that is at least about 50 residues in length, more preferably over a region of at least about 100 residues, and most preferably the sequences are substantially identical over at least about 150 residues. In some embodiments, the sequences are substantially identical over the entire length of the coding regions.

A "subsequence" or "fragment" is any portion of an entire sequence of nucleic acids or amino acids.

The term "genome" refers to the chromosomal nucleic acids of an organism. As used herein, genome also includes the plastid genome (e.g., chloroplast genome, etc.).

The term "*Agrobacterium*" refers to species, subspecies, or strains of the bacterium *Agrobacterium* that are able to mobilize and selectively transfer T-DNA into a plant cell. For example, the *Agrobacterium* is optionally *Agrobacterium rhizogenes*, but more typically is *Agrobacterium tumefaciens*.

The term "callus" refers to an undifferentiated proliferating mass of cells or tissue.

The term "embryogenic cell" refers to a cell from embryogenic tissue or embryogenic callus.

The term "embryogenic callus" refers to tissue or cells that are undifferentiated and without significant structure but with the potential to form a more differentiated tissue (e.g., embryogenic tissue) that can produce embryos and germinate into plants.

The term "embryogenic tissue" refers to tissue having organized structures that include immature somatic embryos. Immature somatic embryos can be matured by culturing them on a maturation medium. Mature somatic embryos can develop into plants upon transfer to a germination medium. A mature somatic embryo is a structure ultimately derived from somatic cells that resembles a zygotic embryo morphologically and developmentally, and that is capable of germinating into a plantlet with both root and shoot poles, when transferred to a suitable growth medium. A "somatic cell" is a cell of a multicellular organism other than gametes.

The term "organogenic cell" refers to a cell from organogenic tissue.

The term "organogenic callus" refers to tissue having an irregular mass of relatively undifferentiated cells, which can arise from, e.g., a single organogenic cell in tissue culture.

The term "organogenic tissue" refers to tissue that is capable of being induced to undergo organogenesis, that is, to form a plant organ such as a shoot, which can then be induced to develop roots to produce a complete plant.

The term "regenerating" or "generating" refers to the formation of a plant that includes a rooted shoot.

The term "effective amount" refers to an amount sufficient to achieve a desired result such as the production of a callus or tissue that is embryogenic or organogenic.

The term "dicot" or "dicotyledonous" refers to plants that produce an embryo with two cotyledons. Exemplary dicots include cotton, soybean, and peanut.

The term "monocot" or "monocotyledonous" refers to plants having a single cotyledon. Exemplary monocots include pineapple, maize, rice, wheat, oat, and barley.

The term "explant" refers to living tissue removed from an organism and placed in a medium for tissue culture.

The term "meristem" refers to a formative plant tissue that comprises cells capable of dividing and giving rise to similar cells or to cells that differentiate to produce tissues and organs.

The term "meristemic cell" refers to a cell from a plant meristem.

The term "non-apical meristemic cell" refers to a meristemic cell that is not from apical meristem, but can be from lateral or axilliary meristems and from cells that upon culture of a non-apical meristem explant have become meristematic.

The term "selecting" refers to a process in which one or more plants or plant cells are identified as having one or more properties of interest, e.g., a selectable marker, enhanced nematode resistance, increased or decreased carotenoid levels, altered coloration, etc. For example, a selection process can include placing organisms under conditions where the growth of those with a particular genotype will be favored. To further illustrate, one can screen a population to determine one or more properties of one or more members of the population. If one or more members of the population is/are identified as possessing a property of interest, it is selected. Selection can include the isolation of a member of a population, but this is not necessary. In addition, selection and screening can be, and often are, simultaneous.

The term "screening" refers to a process for separating a population into different groups. Screening processes typically include determining one or more properties of one or more plants or plant cells. For example, typical screening processes include those in which one or more properties of one or more members of one or more populations is/are determined.

II. Methods of Producing Transformed Plant Cells, Cell Culture, and Explant Sources The present invention relates generally to methods of genetically transforming cells and plants. The methods of the invention are typically more efficient than many pre-existing plant transformation and regeneration techniques. Exemplary plant traits that can be modified using the methods described herein include fruit quality (e.g., sweetness, acidity, texture, condition, color (e.g., shell color or the like), etc.), fruit ripening characteristics, nutritional value (e.g., modified carotenoid levels, etc.), among many other traits typically of interest to consumers. Optionally, other agronomic traits such as, improved flowering control, improved resistance to drought, improved resistance to bacterial diseases, improved resistance to viral diseases, and/or improved resistance to insects, nematodes, and herbicides are also engineered into the cells and plants of the invention. In certain embodiments, the methods of the invention include the use of suitable explant material, which is genetically transformed by contacting the explant material with *Agrobacterium* cells. The *Agrobacterium* cells mediate the transfer of nucleic acid segments, e.g., that encode polypeptides, into plant cells. Other techniques for delivering nucleic acid segments into cells or plants are also optionally utilized. The invention also provides culture media suitable for the steps of inducing the formation of organogenic cells for co-cultivation with *Agrobacterium* cells.

In overview, one aspect of the invention provides a method of producing transformed plant cells that includes culturing at least one non-apical meristemic cell to produce one or more organogenic cells, and introducing at least one nucleic acid segment into the organogenic cells to produce one or more transformed organogenic cells. In another aspect, the invention relates to a method of producing transformed plant cells that includes culturing at least one meristemic cell to produce at least one shoot. In addition, the method also includes culturing at least one explant from the shoot to produce one or more organogenic cells, and introducing at least one nucleic acid segment into the organogenic cells to produce one or more transformed organogenic cells. The methods described herein also typically further include generating at least one plant from the transformed organogenic cells.

The methods of the invention include culturing meristemic cells (e.g., non-apical meristemic cells). In some embodiments, for example, meristemic cells are derived from monocotyledonous plants, whereas in others, meristemic cells are derived from dicotyledonous plants. To further illustrate, meristemic cells are optionally derived from plants selected from the genera: *Ananas, Musa, Vitis, Fragaria, Lotus, Medicago, Onobrychis, Trifolium, Trigonella, Vigna, Citrus, Carica, Persea, Prunus, Syragrus, Theobroma, Coffea, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Mangifera, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucurbita, Cucumis, Browaalia, Lolium, Malus, Apium, Gossypium, Vicia, Lathyrus, Lupinus, Pachyrhizus, Wisteria, Stizolobium, Agrostis, Phleum, Dactylis, Sorguin, Setaria, Zea, Oryza, Triticum, Secale, Avena, Hordeum, Saccharum, Poa, Festuca, Stenotaphrum, Cynodon, Coix, Olyreae, Phareae, Glycine, Pisum, Psidium, Passiflora, Cicer, Phaseolus, Lens, Arachis*, or the like.

To further exemplify, essentially any pineapple variety may be transformed according to the methods described herein. For example, pineapple merstemic cells are optionally obtained from varieties that are typically used for human consumption, including those of the Smooth Cayenne group, the Spanish group (e.g., Red Spanish), the Perolera group, the Pernambuco group, and the Primavera group. The most important variety for use in the production of canned pineapple, other processed pineapple products, and fresh pineapple is typically Smooth Cayenne. Within many of these varieties there are a large number of clones which have been established in different geographical areas, and which are adapted to production in those locations. Among the Smooth Cayenne clones are the Champaka clones which have been used extensively for production of canned and fresh pineapple.

In certain embodiments, rapidly growing shoot cultures are produced in vitro, then explants such as leaf pieces, petioles, cotyledons, stem sections, peduncles, etc. are cultured to produce meristemic or organogenic cells, e.g., in pretreatment processes that prepare cell and/or tissues for cocultivation with *Agrobacterium* cells. Initial explants can be any meristemic region of a plant, including either the main or axillary meristems (apices) of the plant prior to, e.g., flower formation, and the main or axillary meristems of, e.g., the crown of the fruit in pineapple or another plant. These regions can be excised from the plant and sterilized by standard methods as described herein and well known to those of ordinary skill in the art to establish sterile cultures in an artificial medium. Such cultures can be maintained for an extended period of time (e.g., weeks, months or years) by a series of propagation steps. Suitable media for establishment and maintenance of in vitro shoot cultures are described in, e.g., DeWald et al. (1988) *Plant Cell Reports,* 7:535-537; Wakasa et al. (1978) *Japan J Breed* 28:113-121; Mathews and Rangan (1981) *Scientia Hort* 14:227-234; Srinivasa et al. (1981) *Scientia Hort* 15: 23S-238; Fitchet (1990) *Acta Hort* 275:267-274; Bordoloi and Sarma (1993) *J Assam Science Society* 35:41-45; and Firoozabady and Moy (2004) "Regeneration of pineapple plants via somatic embryogenesis and organogenesis," *In Vitro Cellular and Developmental Biology—Plant* 40(1). Additional details relating to culturing plant cells, including pretreatment processes, are provided below in the examples.

One skilled in the art will recognize that many different types of organogenic cells can be used as target cells for the delivery of nucleic acid segments and selection of transformation events. For example, nucleic acid segments can be delivered to the cells of the leaf, leaf base, or stem sections as they undergo organogenesis. In particular, nucleic acid segments can be delivered to organogenic cells after the organogenic material has been maintained and proliferated in vitro for a selected period of time. In certain embodiments, as referred to above, the plant cells which are the target for nucleic acid segment delivery are first obtained from the basal portion of leaves (i.e., leaf base) or sections of the stem of shoots grown in vitro, and proliferated in culture prior to the nucleic acid segment delivery step. As used herein, the term "leaf base" refers to that portion of the leaf that is connected to the stem of a shoot.

Additional details relating to cell culture are described in, e.g., Published International Application No. WO 01/33943, entitled "A METHOD OF PLANT TRANSFORMATION," by Graham et al., which published May 17, 2001, U.S. Pat. No. 5,908,771, entitled "METHOD FOR REGENERATION OF SALVIA SPECIES," which issued Jun. 1, 1999 to Liu et al., U.S. Pat. No. 6,242,257, entitled "TISSUE CULTURE PROCESS FOR PRODUCING A LARGE NUMBER OF VIABLE COTTON PLANTS IN VITRO," which issued Jun. 5, 2001 to Tuli et al., Croy (Ed.) *Plant Molecular Biology Labfax*, Bios Scientific Publishers Ltd. (1993), Jones (Ed.) *Plant Transfer and Expression Protocols*, Humana Press (1995), and in the references cited therein.

Nucleic acid segments can be introduced into cells in a number of art-recognized ways. In overview, suitable methods of transforming plant cells include microinjection (Crossway et al. (1986) *BioTechniques* 4:320-334), electroporation (Riggs et al. (1986) *Proc. Natl. Acad. Sci. USA* 83:5602-5606, *Agrobacterium*-mediated transformation (Hinchee et al. (1988) *Biotechnology* 6:915-921), ballistic particle acceleration or microprojectile bombardment (Sanford et al. U.S. Pat. No. 4,945,050; and McCabe et al. (1988) *Biotechnology* 6:923-926), pollen-mediated delivery (Zhou et al. (1983) *Methods Enzymol.* 101:433, De Wet et al. (1985) in *The Experimental Manipulation of Ovule Tissues*, Chapman et al. (Eds.), Longman, p. 197; Hess (1987) *Intern. Rev. Cytol.* 107:367; and Luo et al. (1989) *Plant Mol. Biol. Rep.* 7:69), direct nucleic acid transfer to protoplasts of pineapple cells (Caboche et al. (1984) *Comptes Rendus Acad. Sci.* 299, series 3:663), microinjection (Crossway et al. (1986) *Mol. Gen. Genet.* 202:179 and Reich et al. (1986) *Bio/technol.* 4:1001), macroinjection of inflorescence (De la Pena et al. (1987) *Nature* 325:274), whisker-mediated impregnation (Dunahay (1993) *Biotechniques* 15:452-460 and Frame et al. (1994) *The Plant Journal* 6:941-948), laser perforation (Weber (1988) *Naturwissenschaften* 75:35), and ultrasonification (Zhang et al. (1991) *Bio/technol.* 9:994).

To further illustrate, *Agrobacterium*-mediated transfer is a widely applicable system for introducing genes into plant cells because the nucleic acid segments can be introduced into whole plant tissues, thereby bypassing the need for regeneration of an intact plant from a protoplast. The use of *Agrobacterium*-mediated expression vectors to introduce DNA into plant cells is well known in the art. See, e.g., the methods described by Fraley et al. (1985) *Biotechnology*, 3:629 and Rogers et al. (1987) *Methods in Enzymology* 153:253-277. Further, the integration of T-DNA is a relatively precise process resulting in few rearrangements. The region of DNA to be transferred is defined by the border sequences, and intervening DNA or nucleic acid segment is usually inserted into the plant genome as described by Spielmann et al. (1986) *Mol. Gen. Genet.*, 205:34 and Jorgensen et al. (1987) *Mol. Gen. Genet.* 207:471.

Many *Agrobacterium* transformation vectors are capable of replication in *E. coli* as well as *Agrobacterium*, allowing for convenient manipulations as described by Klee et al., in *Plant DNA Infectious Agents*, Hohn and Schell, (Eds.), Springer-Verlag (1985) pp. 179-203.

Moreover, recent technological advances in vectors for *Agrobacterium*-mediated gene transfer have improved the arrangement of genes and restriction sites in the vectors to facilitate construction of vectors capable of expressing various polypeptide coding genes. For example, the vectors described by Rogers et al. (1987) *Methods in Enzymology*, 153:253, have convenient multi-linker regions flanked by a promoter and a polyadenylation site for direct expression of inserted polypeptide coding genes and are suitable for present purposes. Suitable vectors are described in greater detail herein.

In certain embodiments of the invention, heterologous nucleic acid segments are introduced using *Agrobacterium* strains carrying the exogenous DNA in a T-DNA element. The recombinant T-DNA element can either be part of a Ti-plasmid that contains the virulence functions necessary for DNA delivery from *Agrobacterium* cells to plant cells, or the T-DNA element can be present on a plasmid distinct from another plasmid carrying the virulence functions (referred to as binary vectors). A variety of these binary vectors, capable of replication in both *E. coli* and *Agrobacterium*, are described in the references cited above. In certain methods of co-cultivation, *Agrobacterium* is grown to a concentration of $2$-$7 \times 10^8$ cells/ml and is diluted to $1$-$6 \times 10^8$ cells/ml, preferably $2$-$5 \times 10^8$ cells/ml before co-cultivation. *Agrobacterium* is typically co-cultivated with plant tissues for about 1-7 days, and more typically for about 2-3 days with, e.g., certain plant tissues, such as pineapple tissues.

Suitable *Agrobacterium* strains include *Agrobacterium tumefaciens* and *Agrobacterium rhizogenes*. While wild-type strains may be used, "disarmed" derivatives of both species, in which the tumor-inducing sequences of the Ti plasmid have been removed, are preferred. Suitable *Agrobacterium tumefaciens* strains include, e.g., EHA101, as described by Hood et al. ((1986) *J. Bacteriol.*, 168:1291-1301), LBA4404, as described by Hoekema et al. ((1983) *Nature*, 303:179-80), and C58(pMP90), as described by Koncz and Schell ((1986) *Mol. Gen. Genet.*, 204:383-96). A preferred *Agrobacterium rhizogenes* strain is 15834, as described by Birot et al. (Biochem, 25: 323-35).

The organogenic cells and tissues and the *Agrobacterium* cells carrying the nucleic acid segment are co-cultivated in a suitable co-cultivation medium to allow transfer of the T-DNA to plant cells. After the *Agrobacterium* strain carrying the nucleic acid segment has been prepared, it is usually cultured prior to incubation with the cells. *Agrobacterium* can be cultured on solid or liquid media according to methods well known to those of skill in the art. See, e.g., U.S. Pat. No. 5,262,316.

As additional options, transformation of plant protoplasts can be achieved using methods based on calcium phosphate precipitation, polyethylene glycol treatment, electroporation, and combinations of these treatments. See, e.g., Potrykus et al. (1985) *Mol. Gen. Genet.*, 199:183; Lorz et al. (1985) *Mol. Gen. Genet.*, 199:178; Fromm et al. (1986) *Nature*, 319:791; Uchimiya et al. (1986) *Mol. Gen. Genet.*, 204:204; Callis et al. (1987) *Genes and Development*, 1:1183; Marcotte et al. (1988) *Nature*, 335:454; Wang et al. (1992) *Bio/Technology* 10:691-696; and Fennell et al. (1992) *Plant Cell Reports*, 11:567-570.

To transform plant species that cannot be successfully regenerated from protoplasts, other ways to introduce nucleic acid segments into intact cells or tissues can be utilized. For example, "particle gun" or high-velocity microprojectile technology can be utilized. Using such technology, nucleic acid segments are carried through the cell wall and into the cytoplasm on the surface of small metal particles as described in Klein et al. (1987) *Nature,* 327:70; Klein et al. (1988) *Proc. Natl. Acad. Sci. U.S.A.,* 85:8502; and McCabe et al. (1988) *Biotechnology,* 6:923; and Vasil et al. (1992) *Bio/Technology,* 9:667-674. The metal particles penetrate through several layers of cells and thus allow for the transformation of cells within tissue explants. Transformation of tissue explants eliminates the need for passage through a protoplast stage and thus speeds the production of transgenic plants.

Nucleic acid segments are also optionally introduced into plants in performing the methods of the invention by direct nucleic acid transfer into pollen as described by Zhou et al. (1983) *Methods in Enzymology* 101:433; Hess (1987) *Intern Rev. Cytol.* 107:367; Luo et al. (1988) *Plant Mol. Biol. Reporter* 6:165. Expression of polypeptide coding genes can be obtained by injection of the nucleic acid segment into reproductive organs of a plant as described by Pena et al. (1987) *Nature* 325:274.

Alternatively, a plant plastid can be transformed directly in performing the methods described herein. Stable transformation of chloroplasts has been reported in higher plants, see, e.g., Svab et al. (1990) *Proc. Nat'l. Acad. Sci. USA* 87:8526-8530; Svab et al. (1993) *Proc. Nat'l Acad. Sci. USA* 90:913-917; Staub et al. (1993) *Embo J.* 12:601-606. The method utilizes particle gun delivery of nucleic acid segments containing a selectable marker and targeting of the nucleic acid to the plastid genome through homologous recombination. In such methods, plastid gene expression can be accomplished by use of a plastid gene promoter or by trans-activation of a silent plastid-borne transgene positioned for expression from a selective promoter sequence such as that recognized by T7 RNA polymerase. The silent plastid gene is activated by expression of the specific RNA polymerase from a nuclear expression construct and targeting of the polymerase to the plastid by use of a transit peptide. Tissue-specific expression may be obtained in such a method by use of a nuclear-encoded and plastid-directed specific RNA polymerase expressed from a suitable plant tissue specific promoter. Such a system has been reported in McBride et al. (1994) *Proc. Natl. Acad. Sci. USA* 91:7301-7305.

After delivery of nucleic acid segments, organogenic cells are typically transferred to media that include a selective agent (e.g., an herbicide or the like) that is capable of preventing the growth of cells that have not received a gene (e.g., a selectable marker) whose expression product is capable of preventing the action of the selective agent to thereby select for transformed plant cells. In certain embodiments, for example, tissues are exposed to sublethal levels of selective agents for about 2-12 weeks, and then to lethal levels of selective agents for about 4-30 weeks in a step-wise selection process. Selectable markers are described further herein. In certain embodiments, organogenic cells are transferred to a recovery medium that comprises counter-selective agents (e.g., antibiotics, etc.), e.g., to kill *Agrobacterium* cells for a period of about 1-15 days, e.g., prior to or concurrently with being transferred to media comprising a selective agent. After a period of culture, organogenic cells that continue to grow normally are separated from cells whose growth has been slowed or terminated.

The regeneration of plants from either single plant protoplasts or various explants is well known in the art. See, e.g., Weissbach et al. (Eds.), *Methods for Plant Molecular Biology,* Academic Press, Inc. (1988). In certain embodiments of the invention, the regeneration and growth process includes the steps of selecting transformed cells and shoots, rooting the transformed shoots, and growing the plantlets in soil. To illustrate, the regeneration of plants containing a gene introduced by *Agrobacterium* from leaf explants can be achieved as described by Horsch et al. (1985) *Science,* 227:1229-1231. In this procedure, transformants are grown in the presence of a selection agent and in a medium that induces the regeneration of shoots in the plant species being transformed as described by Fraley et al. (1983) *Proc. Natl. Acad. Sci. U.S.A.,* 80:4803. This procedure typically produces shoots within two to four weeks and these transformed shoots are then transferred to an appropriate root-inducing medium containing the selective agent and an antibiotic to prevent bacterial growth. In pineapples, for example, leaf bases may be used to produce organogenic materials (Firoozabady and Moy (2004) "Regeneration of pineapple plants via somatic embryogenesis and organogenesis," *In Vitro Cellular and Developmental Biology—Plant* 40(1)), and then these materials may be exposed to *Agrobacterium* to produce, upon selection, transgenic organogenic materials. These materials then are induced to produce shoots and complete plants. Typically, transformed shoots that rooted in the presence of the selective agent to form plantlets are then transplanted to soil or other media to allow the production of additional roots.

Additional details relating to plant regeneration, micropropagation, and other aspects that are adapted for use in the methods of the present invention are provided in, e.g., U.S. Pat. No. 5,952,543 and WO 01/33943 (referenced above), U.S. Pat. Nos. 5,591,616, 6,037,522, European Pat. Application Nos. 604662 (A1) and 672752 (A1), and WO 01/12828. See also, Kyte et al., *Plants from Test Tubes: An Introduction to Micropropagation,* Timber Press, Inc. (1996), Hudson et al., *Hartmann and Kester's Plant Propagation: Principles and Practices* 7$^{th}$ Ed., Pearson Education (2001), Bajaj (Ed.) *High-Tech and Micropropagation I,* Springer-Verlag New York, Inc. (1992), Jain, *In Vitro Haploid Production in Higher Plants,* Kluwer Academic Publishers (1996), and Debergh et al. (Eds.), *Micropropagation: Technology and Application,* Kluwer Academic Publishers (1991).

Optionally, polypeptides produced in transformed cells or plants can be recovered and purified from transformed cell cultures or transformed plant tissues (e.g., fruit tissues or the like) by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. In some cases the protein will need to be refolded to recover a functional product. In addition to the references noted supra, a variety of purification methods are well known in the art, including, e.g., those set forth in Sandana, *Bioseparation of Proteins,* Academic Press, Inc. (1997); and Bollag et al., *Protein Methods* 2nd Ed., Wiley-Liss, NY (1996); Walker, *The Protein Protocols Handbook,* Humana Press, NJ (1996); Harris and Angal, *Protein Purification Applications: A Practical Approach,* IRL Press (1990); Scopes, *Protein Purification: Principles and Practice,* 3rd Ed., Springer Verlag (1993); and Janson et al., *Protein Purification: Principles, High Resolution Methods and Applications,* 2$^{nd}$ Ed., Wiley-VCH (1998).

III. Nucleic Acid Segment Selection

A wide variety of inorganic or organic molecules are optionally introduced into cells using the methods described herein to modify traits as desired. In some embodiments, for example, nucleic acid segments that encode polypeptides (e.g., plant polypeptides, bacterial polypeptides, etc.) are introduced. In certain of these embodiments, the polypeptide is heterologous to the organogenic cells. In some embodiments, the polypeptide is homologous to an endogenous polypeptide of the organogenic cells. Essentially any nucleic acid segment is optionally utilized to transform the organogenic cells according to the methods described herein. Accordingly, no attempt is made to identify all of the known nucleic acids that can be utilized. However, to illustrate, some carotenogenesis-related nucleic acid segments that are optionally introduced into cells or plants typically encode, e.g., isopentenyl diphosphate isomerases, geranylgeranyl pyrophosphate synthases, phytoene synthases, phytoene desaturases, ζ-carotene desaturases, lycopene β-cyclases, lycopene ε-cyclases, β-carotene hydroxylases, ε-hydroxylases, and/or the like. Additional details relating to these carotenogenesis-related nucleic acid segments are described in, e.g., PCT/US03/38664, entitled "TRANSGENIC PINEAPPLE PLANTS WITH MODIFIED CAROTENOID LEVELS AND METHODS OF THEIR PRODUCTION," filed Dec. 5, 2003 by Young et al., which is incorporated by reference. Other exemplary nucleic acid segments optionally comprise or encode, e.g., an ACC synthase, an ACC oxidase, a malic enzyme, a malic dehydrogenase, a glucose oxidase, a chitinase, a defensin, an expansin, a hemicellulase, a xyloglucan transglycosylase, an apetala gene, a leafy gene, a knotted-related gene, a homeobox gene, an Etr-related gene, a ribonuclease, and/or the like.

IV. Artificially Evolved Polypeptides

In certain embodiments of the invention, artificially evolved polypeptides are used to modulate traits in transgenic cells and plants. For example, any of the exemplary target carotenoid biosynthetic polypeptides described above can be artificially evolved to acquire desired traits or properties, such as increased catalytic efficiency, increased substrate specificity, and/or the like. A variety of artificial diversity generating procedures are available and described in the art, which can be used to produce artificially evolved polypeptides. These procedures can be used separately or in combination to produce variants of a nucleic acid, as well as variants of proteins encoded by the nucleic acid variants. Individually and collectively, these procedures provide robust, widely applicable ways of engineering or rapidly evolving individual nucleic acids and proteins, or even entire biochemical pathways or selected portions of such pathways. The products of these procedures can be used in the transformation methods of the invention.

In particular, the result of any of the diversity generating procedures described herein or otherwise known in the art can be the generation of one or more nucleic acids that are typically selected or screened for nucleic acids encoding enzymes with or which confer desirable properties, such as increased catalytic efficiency, etc. This can include identifying any activity that can be detected, for example, in an automated or automatable format, by any of the assays known in the art. A variety of related (or even unrelated) properties can be evaluated, in serial or in parallel, at the discretion of the practitioner.

Artificially evolved polypeptides that are optionally used in the methods of the present invention can be derived using many different techniques. To illustrate, chimeric enzymes including identifiable components (e.g., protein domains) derived from two or more parental sequences can be utilized. For example, domains in different phytoene synthases can be identified and selected for inclusion in a chimeric progeny phytoene synthase. Various sequence comparison algorithms and other tools that are useful for chimeric enzyme design are described further below.

Artificially evolved enzymes can additionally be developed using various mutagenic methods, such as cassette mutagenesis, site-directed mutagenesis (see, e.g., Botstein & Shortle (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)), chemical mutagenesis, error-prone PCR, site-saturation mutagenesis, recursive ensemble mutagenesis, and the like. To illustrate, error-prone PCR can be used to generate nucleic acid variants. Using error-prone PCR, for example, PCR is performed under conditions where the copying fidelity of the DNA polymerase is low, such that a high rate of point mutations is obtained along the entire length of the PCR product. Examples of such techniques are described further in, e.g., in Leung et al. (1989) *Technique* 1:11-15 and Caldwell et al. (1992) *PCR Methods Applic.* 2:28-33. To further illustrate an exemplary mutagenic technique, cassette mutagenesis is optionally used in a process that replaces a small region of a double stranded DNA molecule with, e.g., a synthetic oligonucleotide cassette that differs from the native sequence. The synthetic oligonucleotide can contain, e.g., completely and/or partially randomized native sequence(s). Additional details relating to cassette mutagenesis are described in, e.g., Wells et al. (1985) "Cassette mutagenesis: an efficient method for generation of multiple mutations at defined sites" *Gene* 34:315-323. Another exemplary method of creating molecular diversity mutagenically is a recursive ensemble mutagenesis process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin et al. (1992) *Proc. Natl. Acad. Sci. USA* 89:7811-7815. The mutagenic techniques referred to above are provided simply to illustrate certain procedures that are optionally used to produce diversity in nucleic acids that encode polypeptides. Many other approaches to creating diversity via mutagenesis are well-known and are also suitable for the methods of the present invention.

Nucleic acids that encode polypeptides, such as those described above, are also optionally used as substrates for a variety of recombination reactions, such as a recursive sequence recombination protocol. Many of these techniques are described in various publications including, e.g., Chang et al. (1999) "Evolution of a cytokine using DNA family shuffling" *Nature Biotechnology* 17:793-797, Crameri et al. (1998) "DNA shuffling of a family of genes from diverse species accelerates directed evolution" *Nature* 391:288-291, Crameri et al. (1997) "Molecular evolution of an arsenate detoxification pathway by DNA shuffling," *Nature Biotechnology* 15:436-438, Crameri et al. (1996) "Improved green fluorescent protein by molecular evolution using DNA shuffling" *Nature Biotechnology* 14:315-319, Stemmer (1995) "Searching Sequence Space" *Bio/Technology* 13:549-553, and Stemmer (1994) "Rapid evolution of a protein in vitro by DNA shuffling" *Nature* 370:389-391.

Many of the diversity generating procedures described above (e.g., chimeric enzyme design and synthesis, recursive sequence recombination, etc.), include determining levels of homology among starting sequences. For example, in the processes of sequence comparison and homology determination, one sequence, e.g., one fragment or subsequence of a gene sequence to be recombined, can be used as a reference against which other test nucleic acid sequences are compared. This comparison can be accomplished with the aid of a sequence comparison algorithm or by visual inspection. When an algorithm is employed, test and reference sequences are input into a computer, subsequence coordinates are designated, as necessary, and sequence algorithm program parameters are specified. The algorithm then calculates the percent sequence identity for the test nucleic acid sequence(s) relative to the reference sequence, based on the specified program parameters.

For purposes of the present invention, suitable sequence comparisons can be executed, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection. See generally, *Current Protocols in Molecular Biology*, F. M. Ausubel et al., eds., Current Protocols, a joint venture between Greene Publishing Associates, Inc. and John Wiley & Sons, Inc., (supplemented through 2001). Another example search algorithm that is suitable for determining percent sequence identity and sequence similarity is the Basic Local Alignment Search Tool (BLAST) algorithm, which is described in, e.g., Altschul et al. (1990) *J. Mol. Biol.* 215:403-410. Software for performing BLAST analyses is publicly available through the National Center for Biotechnology Information on the world wide web at ncbi.nlm.nih.gov.

Kits for mutagenesis, library construction and other diversity generation methods are commercially available. For example, kits are available from, e.g., Stratagene (e.g., QuickChange™ site-directed mutagenesis kit, and Chameleon™ double-stranded, site-directed mutagenesis kit), Bio/Can Scientific, Bio-Rad (e.g., using the Kunkel method referred to above), Boehringer Mannheim Corp., Clonetech Laboratories, DNA Technologies, Epicentre Technologies (e.g., 5 prime 3 prime kit), Genpak Inc., Lemargo Inc., Life Technologies (Gibco BRL), New England Biolabs, Pharmacia Biotech, Promega Corp., Quantum Biotechnologies, Amersham International plc, and Anglian Biotechnology Ltd.

V. Nucleic Acid Segment Preparation

Nucleic acid segments used in the methods of the invention, such as those described above, can be prepared using various methods or combinations thereof, including certain DNA synthetic techniques, DNA amplification, nuclease digestion, etc. Searchable sequence information that is available from nucleic acid databases can be utilized during nucleic acid segment and vector selection and/or design processes. Genbank®, Entrez®, EMBL, DDBJ, GSDB, NDB and the NCBI are examples of public database/search services that can be accessed. These databases are generally available via the internet or on a contract basis from a variety of companies specializing in genomic information generation and/or storage. These and other helpful resources are readily available and known to those of skill.

The sequence of a polynucleotide to be used in any of the methods of the present invention can also be readily determined using techniques well-known to those of skill, including Maxam-Gilbert, Sanger Dideoxy, and Sequencing by Hybridization methods. For general descriptions of these processes consult, e.g., Stryer, *Biochemistry*, 4$^{th}$ Ed., W.H. Freeman and Company (1995) and Lewin, *Genes VI*, Oxford University Press (1997). See also, Maxam and Gilbert (1977) "A New Method for Sequencing DNA," *Proc. Natl. Acad. Sci.* 74:560-564, Sanger et al. (1977) "DNA Sequencing with Chain-Terminating Inhibitors," *Proc. Natl. Acad. Sci.* 74:5463-5467, Hunkapiller et al. (1991) "Large-Scale and Automated DNA Sequence Determination," *Science* 254:59-67, and Pease et al. (1994) "Light-Generated Oligonucleotide Arrays for Rapid DNA Sequence Analysis," *Proc. Natl. Acad. Sci.* 91:5022-5026.

Nucleic acid segments can also be synthesized by chemical techniques, for example, utilizing the phosphotriester method of Matteucci et al. (1981) *J. Am. Chem. Soc.* 103:3185. Of course, by chemically synthesizing the coding sequence, any desired modifications can be made simply by substituting the appropriate bases for those encoding the native amino acid residue sequence. Furthermore, nucleic acid segments are optionally obtained from existing recombinant DNA molecules (plasmid vectors) containing those genes. Certain of these plasmids are available from the American Type Culture Collection (ATCC), 12301 Parklawn Drive, Rockville, Md., 20852.

The nucleic acid segments and constructs or vectors optionally utilized in performing the methods of the invention can also be prepared by a number of other techniques known in the art, such as molecular cloning techniques. A wide variety of cloning and in vitro amplification methods suitable for the construction of recombinant nucleic acids, such as expression vectors, are well-known to persons of skill. Vectors suitable for use in the present invention are described further below. General texts which describe molecular biological techniques useful herein, including mutagenesis, include Berger and Kimmel, *Guide to Molecular Cloning Techniques, Methods in Enzymology*, Vol. 152, Academic Press, Inc. (1999) ("Berger"); Sambrook et al., *Molecular Cloning—A Laboratory Manual* 2nd Ed., Vol. 1-3, Cold Spring Harbor Laboratory (2000) ("Sambrook"); and *Current Protocols in Molecular Biology*, Ausubel et al. (Eds.), Current Protocols, a joint venture between Greene Publishing Associates, Inc. and John Wiley & Sons, Inc., (supplemented through 2000) ("Ausubel"). Examples of techniques sufficient to direct persons of skill through in vitro amplification methods, including the polymerase chain reaction (PCR), the ligase chain reaction (LCR), Qβ-replicase amplification and other RNA polymerase mediated techniques (e.g., NASBA) are found in Berger, Sambrook, and Ausubel, as well as Mullis et al. (1987) U.S. Pat. No. 4,683,202; *PCR Protocols A Guide to Methods and Applications* (Innis et al., eds.), Academic Press Inc. (1990) ("Innis"); Arnheim & Levinson (1990) *Chemical and Engineering News* 36-47; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.* 35:1826; Landegren et al., (1988) *Science* 241:1077-1080; Van Brunt (1990) *Biotechnology* 8:291-294; Wu and Wallace, (1989) *Gene* 4:560; Barringer et al. (1990) *Gene* 89:117, and Sooknanan and Malek (1995) *Biotechnology* 13:563-564. Additional methods of cloning in vitro amplified nucleic acids are also described in U.S. Pat. No. 5,426,039 to Wallace et al. Methods of amplifying large nucleic acids by PCR are summarized in Cheng et al. (1994) *Nature* 369:684-685 and the references cited therein, in which PCR amplicons of up to 40 kb are generated. One of skill will also appreciate that essentially any RNA can be converted into a double stranded DNA suitable for restriction digestion, PCR expansion and sequencing using reverse transcriptase and a polymerase. See, Ausubel, Sambrook and Berger, all supra.

The isolation of a nucleic acid sequence for inclusion in a vector construct utilized in certain embodiments of the methods of the invention may be accomplished by any number of techniques known in the art. For instance, oligonucleotide probes based on known sequences can be used to identify the desired gene in a cDNA or genomic DNA library. Probes may be used to hybridize with genomic DNA or cDNA sequences to isolate homologous genes in the same or different species. Alternatively, antibodies raised against an enzyme can be used to screen an mRNA expression library for the corresponding coding sequence.

Alternatively, the nucleic acids of interest (e.g., genes encoding desired polypeptides) can be amplified from nucleic acid samples using amplification techniques. For instance, polymerase chain reaction (PCR) technology can be used to amplify the sequences of desired genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR, see Innis, supra.

Polynucleotides may also be synthesized by well-known techniques as described in the technical literature. See, e.g., Carruthers et al. (1982) *Cold Spring Harbor Symp. Quant. Biol.* 47:411-418, and Adams et al. (1983) *J. Am. Chem. Soc.* 105:661. Double stranded DNA segments may then be obtained either by synthesizing the complementary strand and annealing the strands together under appropriate conditions, or by adding the complementary strand using DNA polymerase with an appropriate primer sequence.

Oligonucleotides for use as probes, e.g., in in vitro amplification methods, for use as gene probes are typically synthesized chemically according to the solid phase phosphoramidite triester method described by Beaucage and Caruthers (1981) *Tetrahedron Letts.* 22(20):1859-1862, e.g., using an automated synthesizer, as described in Needham-VanDevanter et al. (1984) *Nucleic Acids Res.* 12:6159-6168. Oligonucleotides for use in the nucleic acid constructs or vectors that are utilized in certain embodiments of the invention can also be custom made and ordered from a variety of commercial sources known to persons of skill.

VI. Vectors

Essentially any vector or vector system can be used to create the transformed plants and organogenic cells of the invention. In certain embodiments, nucleic acid segments that encode polypeptides are operatively linked to vectors in the form of plasmids or plasmid systems (e.g., binary systems, trinary systems, shuttle vector systems, etc.). Certain exemplary plasmid systems that are optionally adapted for use in the present invention are described in, e.g., U.S. Pat. No. 5,977,439 to Hamilton (issued Nov. 2, 1999), U.S. Pat. No. 5,929,306 to Torisky et al. (issued Jul. 27, 1999), U.S. Pat. No. 5,149,645 to Hoekema et al. (issued Sep. 22, 1992), U.S. Pat. No. 6,165,780 to Kawasaki (issued Dec. 26, 2000), U.S. Pat. No. 6,147,278 to Rogers et al. (issued Nov. 14, 2000), U.S. Pat. No. 4,762,785 to Comai (issued Aug. 9, 1988), and U.S. Pat. No. 5,068,193 to Comai (issued Nov. 26, 1991).

The nucleic acid segments optionally utilized herein, e.g., in the form of expression cassettes typically include in the 5'-3' direction of transcription, a transcriptional and translational initiation region, a DNA sequence of interest (e.g., a gene encoding a polypeptide), and a transcriptional and translational termination region functional in the particular plant being transformed. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991), *Mol. Gen. Genet.*, 262:141-144; Proudfoot, (1991), *Cell,* 64:671-674; Sanfacon et al., (1991), *Genes Dev.,* 5:141-149; Mogen et al., (1990), *Plant Cell,* 2:1261-1272; Munroe et al., (1990), *Gene,* 91:151-158; Ballas et al., (1989), *Nucleic Acids Res.* 17:7891-7903; and Joshi et al., (1987), *Nucleic Acid Res.*, 15:9627-9639).

In certain embodiments, the nucleic acid segments of interest will be targeted to plastids, such as chloroplasts, for expression. In this manner, where the nucleic acid segment is not directly inserted into the plastid, the expression cassette will additionally contain a gene encoding a transit peptide to direct the nucleic acid of interest to the plastid. Such transit peptides are known in the art. See, e.g., Von Heijne et al. (1991) *Plant Mol. Biol. Rep.* 9:104-126; Clark et al. (1989) *J. Biol. Chem.* 264:17544-17550; della-Cioppa et al. (1987) *Plant Physiol.* 84:965-968; Romer et al. (1993) *Biochem. Biophys. Res Commun.* 196:1414-1421; and, Shah et al. (1986) *Science* 233:478481. Plant genes useful in the invention may utilize native or heterologous transit peptides.

Constructs optionally utilized in performing the methods of the invention may also include any other necessary regulators such as plant translational consensus sequences (Joshi, C. P., (1987), *Nucleic Acids Research,* 15:6643-6653), introns (Luehrsen and Walbot, (1991), *Mol. Gen. Genet.*, 225:81-93) and the like, operably linked to the nucleotide sequence of interest.

In some embodiments, 5' leader sequences are included in expression cassette constructs utilized in performing the methods of the invention. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) (Allison et al., (1986); MDMV leader (Maize Dwarf Mosaic Virus); Virology, 154:9-20), and human immunoglobulin heavy-chain binding protein (BP), (Macejak, D. G., and Sarnow, P., (1991), *Nature,* 353:90-94; untranslated leader from the coat protein mRNA of alfalfa mosaic virus (AMV RNA 4), (Jobling, S. A., and Gehrke, L., (1987), *Nature,* 325:622-625; tobacco mosaic virus leader (TMV), (Gallie, D. R. et al., (1989), *Molecular Biology of RNA*, pages 237-256; and maize chlorotic mottle virus leader (MCMV) (Lommel, S. A. et al., (1991), *Virology,* 81:382-385. See also, Della-Cioppa et al., (1987), *Plant Physiology,* 84:965-968.

Depending upon where the DNA sequence of interest is to be expressed, it may be desirable to synthesize the sequence with plant preferred codons, or alternatively with chloroplast preferred codons. Plant preferred codons may be determined from the codons of highest frequency in the proteins expressed in the largest amount in the particular plant species of interest. See, European Patent Application Nos. 0359472 and 0385962; International Application No. WO 91/16432; Perlak et al. (1991) *Proc. Natl. Acad. Sci. USA* 88:3324-3328; and Murray et al. (1989) *Nucleic Acids Res.* 17: 477-498. In this manner, the nucleotide sequences can be optimized for expression in plants of interest. It is recognized that all or any part of the gene sequence may be optimized or synthetic. That is, synthetic or partially optimized sequences may also be used. For the construction of chloroplast preferred genes, see e.g., U.S. Pat. No. 5,545,817.

In preparing expression cassettes, the various nucleic acid fragments may be manipulated, so as to provide for the nucleic acid sequences in the proper orientation and, as appropriate in the proper reading frame. Towards this end, adapters or linkers may be employed to join the nucleic acid fragments or other manipulations may be involved to provide for convenient restriction sites, removal of superfluous nucleic acid segments, removal of restriction sites, or the like. For this purpose, in vitro mutagenesis, primer repair, restriction, annealing, resection, ligation, or the like may be employed, where insertions, deletions or substitutions, e.g., transitions and transversions, may be involved.

The vectors optionally utilized in performing the methods described herein may include expression control elements, such as promoters. Polypeptide coding genes are operatively linked to the expression vector to permit the promoter sequence to direct RNA polymerase binding and expression of the polypeptide coding gene. Useful in expressing the polypeptide coding gene are promoters which are inducible, viral, synthetic, constitutive as described in, e.g., Poszkowski et al. (1989) *EMBO J.* 3:2719 and Odell et al. (1985) *Nature* 313:810 (1985), and temporally regulated, spatially regulated, and spatiotemporally regulated as described in, e.g., Chua et al. (1989) *Science* 244:174-181.

The choice of which expression vector and, e.g., to which preselected organ-enhanced promoter a polypeptide coding gene is operatively linked typically depends on the functional properties desired, e.g., the location and timing of protein expression. A vector that is useful in practicing the present invention integrates into the genome of the plant of interest, is capable of directing the replication, and also the expression of the polypeptide coding gene included in the nucleic acid segment to which it is operatively linked. It is well known in the art that the entire expression vector does not integrate into the host plant genome, but only a portion integrates. Nonetheless, the vector will be said to integrate for ease of expression.

In some embodiments, a construct utilized in performing the methods of the invention may include elements in addition to the conjoined nucleic acid sequences, such as promoters, enhancer elements, and signaling sequences. Exemplary promoters include the CaMV promoter, a promoter from the ribulose-1,5-bisphosphate carboxylase-oxygenase small subunit gene, a ubiquitin promoter, and a rolD promoter. Exemplary enhancer elements are described in, e.g., U.S. Pat. No. 6,271,444, which issued Aug. 7, 2001 to McBride et al. Exemplary signaling sequences include, but are not limited to, nucleic acid sequences encoding tissue-specific transit peptides, such as chloroplast transit peptides (see, e.g., Zhang et al. (2002) *Trends Plant Sci* 7(1):14-21).

In certain embodiments, a strongly or weakly constitutive plant promoter can be employed which will direct expression of the encoded sequences in all tissues of a plant. Such promoters are active under most environmental conditions and states of development or cell differentiation. Examples of constitutive promoters include the 1'- or 2'-promoter derived from T-DNA of *Agrobacterium tumefaciens*, and other transcription initiation regions from various plant genes known to those of skill. In situations in which overexpression of a gene is undesirable, a weak constitutive promoters can be used for lower levels of expression. In instances where high levels of expression are sought, a strong promoter, e.g., a t-RNA or other pol III promoter, or a strong pol II promoter, such as the cauliflower mosaic virus promoter, can be used.

Alternatively, a plant promoter may be under environmental control. Such promoters are referred to here as "inducible" promoters. Examples of environmental conditions that may effect transcription by inducible promoters include pathogen attack, anaerobic conditions, or the presence of light.

In some embodiments, promoters incorporated into a construct optionally used to perform the methods of the present invention are "tissue-specific" and, as such, under developmental control in that the desired gene is expressed only in certain tissues, such as fruit-tissues. In embodiments in which one or more nucleic acid sequences endogenous to the plant are incorporated into a construct, the endogenous promoters (or variants thereof) from these genes can be employed for directing expression of the genes in the transformed plant. Tissue-specific promoters can also be used to direct expression of heterologous structural genes, including the artificially evolved nucleic acids described herein.

In addition to the promoters noted above, promoters of bacterial origin which operate in plants include the octopine synthase promoter, the nopaline synthase promoter and other promoters derived from native Ti plasmids (see, Herrara-Estrella et al. (1983) *Nature* 303:209-213). Viral promoters include the 35S and 19S RNA promoters of cauliflower mosaic virus (Odell et al. (1985) *Nature* 313:810-812). Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315-3327.

In preparing constructs utilized in performing the methods of the invention, sequences other than the promoter and the conjoined nucleic acid segment can also be employed. If normal polypeptide expression is desired, a polyadenylation region at the 3'-end of the coding region can be included. The polyadenylation region can be derived from the natural gene, from a variety of other plant genes, or from T-DNA.

Typical vectors useful for expression of genes in plants are well known in the art and include vectors derived from the tumor-inducing (Ti) plasmid of *Agrobacterium tumefaciens* described by Rogers et al. (1987) *Meth. in Enzymol.*, 153: 253-277 (1987). These vectors are plant integrating vectors in that on transformation, the vectors integrate a portion of vector DNA into the genome of the plant. For integrating vectors based on the Ti plasmid, the region integrated into the host plant chromosomes is that between the right and left borders of the Ti plasmid.

Exemplary *A. tumefaciens* vectors useful herein are plasmids pKYLX6 and pKYLX7 of Schardl et al. (1987) *Gene* 61:1-11 and Berger et al. (1989) *Proc. Natl. Acad. Sci. U.S.A.*, 86:8402-8406. Plasmid pKYLX6 is an *E. coli* vector designed for intermediate constructs, whereas plasmid pKYLX7 is an *A. tumefaciens* vector designed for integration of cloned genes. Modified vectors pKYLX61 and pKYLX71 contain HindIII, XhoI, BamHI, PstI and SstI sites in place of the original HindIII-SstI fragment multiple cloning site region. Another useful vector herein is plasmid pBI101.2 that is available from Clontech Laboratories, Inc., Palo Alto, Calif. Plasmids pKYLX7, pKYLX71 and pB7101.2 are binary vectors that are used in *A. tumefaciens* with another vector having a vir gene. Additional details relating to binary vectors are described in, e.g., Hellens et al. (2000) "pGREEN: a versatile and flexible Ti vector for *Agrobacterium*-mediated plant transformation," *Plant Molecular Biology* 42:819-832. Other vectors systems are also optionally utilized herein including, e.g., trinary vector systems. Another plant transformation system is based on *Agrobacterium rhizogenes* that induces hairy roots rather than a tumor on transformation. See, e.g., International Publication No. WO 88/02405 (published Apr. 7, 1988) describes the use of *A. rhizogenes* strain A4 and its Ri plasmid along with *A. tumefaciens* vectors pARC8 or pARC16 to transform plants. *Agrobacterium*-mediated transformation is described further below.

Retroviral expression vectors are also optionally adapted for use in performing the methods described herein. The term "retroviral expression vector," as used herein, refers to a DNA molecule that includes a promoter sequence derived from the long terminal repeat (LTR) region of a retrovirus genome. Because some of the nucleic acid segment expression products that may be utilized herein are associated with food production and coloration, the retroviral expression vector is preferably replication-incompetent in eukaryotic cells. The construction and use of retroviral vectors has been described by, e.g., Verma in International Publication No. WO 87/00551, and in Cocking et al. (1987) *Science* 236:1259-62.

In some embodiments, the vector used to express a polypeptide coding gene includes a plant selectable marker that confers a selectable phenotype on the transformed cell. The selectable plant marker gene on the DNA segment to be inserted will usually encode a function, which permits the survival and emergence of transformed organogenic cells or tissue in a selective medium. Usually, the selectable marker gene will encode antibiotic resistance, with suitable genes including those coding for resistance to the antibiotic spectinomycin (e.g., the aadA gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron. Selection based on resistance to sulfonylurea-type herbicides is preferred. Selectable markers based on the green fluorescent protein (GFP) or β-glucuronidase (GUS) are also optionally used and are described further in, e.g., Mantis et al. (2000) "Comparing the utility of β-glucuronidase and green fluorescent protein for detection of weak promoter activity in *Arabidopsis thaliana*," *Plant Molecular Biology Reporter* 18:319-330.

Methods to select transformed plant cells incorporating a desired resistance gene are well known in the art. For example, if the marker is sulfonylurea resistance, the selection medium generally contains a sulfonylurea-type herbicide at an appropriate concentration (e.g., chlorsulfuron in the range of about 1-1000 μg/l, and more typically in the range of about 5-100 μg/l). For selection of geneticin resistant plant cells or tissue, which contain the NPTII gene, geneticin is typically included in the medium at 10-50 mg/l. Spectinomycin resistant plant cells or tissue containing the aadA gene are typically selected on medium containing 200-1000 mg/l spectinomycin.

In certain embodiments, transformed cells and plants are selected according to visual differentiation. For example, since many carotenoids are colored, these carotenoid products can be visualized and determined by their characteristic spectra and other analytic methods. Therefore, genes encoding carotenoid biosynthetic enzymes may be used as marker genes to allow for visual selection of transformants. In particular, such transformed cells generally display colors ranging from yellow to orange to red as a result of the increased carotenoid levels. In some embodiments, other analytical techniques can be used to select transformed cells including, e.g., mass spectrometry, thin layer chromatography (TLC), high pressure liquid chromatography (HPLC), capillary electrophoresis (CE), NMR spectroscopy, and conventional hybridization techniques.

VII. Plant Trait Modulation Strategies

The nucleic acid segments introduced into organogenic cells as described herein may contain one or more genes that are chosen to provide new plant traits, to enhance an existing plant trait, or to otherwise modify expression of phenotypes exhibited by the plant. Such traits include herbicide resistance, pesticide resistance, disease resistance, environmental tolerance (e.g., heat, cold, drought, salinity), morphology, growth characteristics, nutritional content, taste, yield, horticultural characteristics, consumer (quality) traits, and the like.

Functional genes to be introduced may be structural genes, which encode polypeptides that impart the desired phenotype. Alternatively, functional genes may be regulatory genes that play roles in transcriptional and/or translational control to suppress, enhance, or otherwise modify the transcription and/or expression of endogenous genes within the plants. In some embodiments, for example, introduced nucleic acid segments encode polypeptide transcription factors, which when expressed in transformed cells effect elevated expression of targeted genes. In other embodiments, introduced nucleic acid segments encode promoters and/or enhancers, which nucleic acid segments homologously recombine with promoters and/or enhancers of endogenous genes to increase or decrease expression of the genes as desired.

To further illustrate, various nucleic acid constructs can be used in a number of techniques to suppress expression of endogenous plant genes, e.g., sense or antisense suppression or ribozymes. Anti-sense RNA inhibition of gene expression has been shown; see, e.g., Sheehy et al. (1988) *Proc. Nat. Acad. Sci. USA* 85:8805-8809, and Hiatt et al. U.S. Pat. No. 4,801,340. For examples of the use of sense suppression to modulate expression of endogenous genes see, Napoli et al. (1990) *The Plant Cell* 2:279-289, and U.S. Pat. No. 5,034,323.

Catalytic RNA molecules or ribozymes can also be used to inhibit gene expression, which is optionally used to effect the accumulation of selected products that are upstream in a given biochemical pathway from the gene that is inhibited. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified, which are optionally adapted for use in performing the methods described herein. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus, and subterranean clover mottle virus. The design and use of target RNA-specific ribozymes is described in Haseloff et al. (1988) *Nature* 334:585-591.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

To further illustrate, RNA interference (RNAi), also known as Post-Transcriptional Gene Silencing (PTGS), is also optionally utilized to modulate traits in plants. RNAi is a cellular mechanism that selectively negates the effect of a target gene by destroying messenger RNA. By destroying the targeted mRNA, protein synthesis is interrupted, thereby effectively "silencing" the target gene. In certain embodiments, this process is initiated by double-stranded RNA (dsRNA), where one strand is substantially identical to the target mRNA sequence. Accordingly, in some embodiments of the invention, nucleic acid segments introduced into plant cells as described herein trigger the production of double stranded dsRNA, which is then cleaved into small interfering RNA (siRNA) as part of the RNAi process. This results in the destruction of the target mRNA, thereby effectively silencing expression of the target gene. Additional details relating to RNAi are described in, e.g., U.S. Pat. No. 6,573,099, entitled "GENETIC CONSTRUCTS FOR DELAYING OR REPRESSING THE EXPRESSION OF A TARGET GENE," which issued Jun. 3, 2003 to Graham, and in, e.g., Arenz et al. (2003) "RNA interference: from an ancient mechanism to a state of the art therapeutic application?" *Naturwissenschaften.* 90(8):345-59, Wang et al. (2003) "RNA interference: antiviral weapon and beyond," *World J Gastroenterol.* 9(8):1657-61, and Lavery et al. (2003) "Antisense and RNAi: powerful tools in drug target discovery and validation" *Curr Opin Drug Discov Devel.* 6(4):561-9. Custom nucleic acid segments that can be utilized to effect target gene silencing are also commercially available from various suppliers, such as Ambion, Inc. (Austin, Tex., USA), Benitec Australia Limited (St Lucia, AU), and the like.

Often the functional genes to be introduced will be modified from their native form. For example, sense and anti-sense constructs referred to above often have all or a portion of the transcript of the native gene operably linked to a promoter sequence at the 5' end of the transcribable segment, and operably linked to the 3' sequence of another gene (including polyadenylation sequences) at the 3' end of the transcribable segment. As is apparent to those skilled in the art, the promoter sequence could be one of the many plant active sequences already described. Alternatively, other plant-active promoter sequences can be derived specifically to be linked to the transcribable segment. The promoter can be endogenous to pineapple, or can be from an exogenous source such as a cauliflower mosaic virus 35S promoter (Odell et al. (1985) *Nature* 313:810-812), the ubiquitin 1 promoter (Christiensen et al. (1992) *Plant Mol. Biol.* 18:675-689), or the Smas promoter (Ni et al. (1995) *Plant J.* 7:661-676). The 3' end sequence to be added can be derived from, preferably, the nopaline synthase or octopine synthase genes, or alternatively from another plant gene, or less preferably from any other eukaryotic gene.

As described herein, the production of carotenoids can be elevated in cells and plants transformed with nucleic acid segments (e.g., a first gene of interest) that, e.g., encode carotenoid biosynthetic enzymes. Optionally, once this biosynthetic activity has been increased by expression of these introduced carotenoid biosynthesis genes, the pathway can be diverted for the production and accumulation of specific carotenoids. The diversion typically includes the use of at least one second gene of interest. To illustrate, the second gene can encode an enzyme to force the production of a particular carotenoid or alternatively can encode a gene to stop the pathway for the accumulation of a particular carotenoid. To force the production of a particular carotenoid, expression of a carotenoid biosynthesis gene in the pathway for the desired carotenoid is used. Genes native or exogenous to the target plant are optionally used in these methods, including, e.g., carotenoid biosynthesis genes from sources other than plants, such as bacteria, including *Erwinia* and *Rhodobacter* species. Exemplary carotenoid biosynthesis genes that can be utilized for these purposes are described further above. To stop the pathway in order to accumulate a particular carotenoid compound, the second gene will provide for inhibition of transcription of a gene (e.g., native or exogenous) to the target plant in which the enzyme encoded by the inhibited gene is capable of modifying the desired carotenoid compound. Inhibition may be achieved by transcription of the gene to be inhibited in either the sense (cosuppression) or antisense orientation of the gene. Other sense and antisense strategies for modulating carotenoid accumulation in plants are referred to above.

To further illustrate, but not to limit the present invention, to alter, e.g., the carotenoid composition of a plant towards the accumulation of higher levels of β-carotene derived carotenoids, such as zeaxanthin, zeaxanthin diglucoside, canthaxanthin, and astaxanthin, inhibition of lycopene ε-cyclase can be achieved to prevent accumulation of α-carotene and other carotenoids that are derivative from α-carotene, such as lutein. In addition to the inhibition of lycopene ε-cyclase, increased expression of a second gene may be utilized for increased accumulation of a particular β-carotene derived carotenoid. For example, increased β-carotene hydroxylase expression is useful for production of zeaxanthin, whereas increased β-carotene hydroxylase and keto-introducing enzyme expression is useful for production of astaxanthin. Alternatively, to accumulate lycopene, the inhibition of lycopene β-cyclase or of lycopene ε-cyclase and lycopene β-cyclase can be effected to reduce conversion of lycopene to α- and β-carotene.

A variety of genes are optionally used as to divert carotenoid biosynthesis in cells and plants as desired. These include, but are not limited to, β-carotene hydroxylase or crtZ (Hundle et al. (1993) *FEBS Lett.* 315:329-334, Accession No. M87280) for the production of zeaxanthin; genes encoding keto-introducing enzymes, such as crtW (Misawa et al. (1995) *J. Bacteriol.* 177:6575-6584, WO 95/18220, WO 96/06172) or β-C-4-oxygenzse (crtO; Harker et al. (1997) *FEBS Lett.* 404:129-134) for the production of canthaxanthin; crtZ and crtW or crtO for the production of astaxanthin; ε-cyclase and ε-hydroxylase for the production of lutein; ε-hydroxylase and crtZ for the production of lutein and zeaxanthin; antisense lycopene ε-cyclase (Accession No. U50738) for increased production of β-carotene; antisense lycopene ε-cyclase and lycopene β-cyclase (Hugueney et al. (1995) *Plant J.* 8:417-424, Cunningham Jr et al. (1996) *Plant Cell* 8:1613-1626, Scolnik et al. (1995) *Plant Physiol.* 108:1343, Accession Nos. X86452, L40176, X81787, U50739 and X74599) for the production of lycopene; antisense plant phytoene desaturase for the production of phytoene; and the like.

In this manner, the pathway can be modified for the high production of any particular carotenoid compound of interest. Such compounds include, but are not limited to, α-cryptoxanthin, γ-cryptoxanthin, ζ-carotene, phytofluene, neurosporane, etc. Using the methods of the invention, any compound of interest in the carotenoid pathway can be produced at high levels in selected storage organs, such as the fruit of plants.

Optionally, the pathway can also be manipulated to decrease levels of, for example, a particular carotenoid by, e.g., transforming the plant cell with antisense DNA sequences which prevents the conversion of the precursor compound into the particular carotenoid being regulated.

Although some of the description herein relates to altering the accumulation of carotenoids in plants for purposes of clarity of illustration, it will be appreciated that the general strategies described herein can be readily adapted to modulate other plant traits by persons skilled in the art. Accordingly, the present invention is not limited to modulated carotenoid accumulation in plants.

VIII. Examples

The following examples are offered to illustrate, but not to limit the claimed invention.

Media are designated with letters and numbers; letters refer to media components used, followed by a number that indicates the concentration of the particular component. For example, B2N2 is an MS media that contains 6-benzylamino purine (BA or B) and α-naphthalene acetic acid (NAA or N). More specific details relating to the media compositions referred to in these examples, including component concentrations, are provided below.

Example 1

Transformation and Regeneration of Pineapple Del Monte Gold MD-2 Using *Agrobacterium tumefaciens* Strain C58PMP90/PDM 1. Preparation of Source Tissues (Transgenic Line 2.48.5.1)
   i. Establishment of Shoot Cultures.

Meristems isolated from crowns of Del Monte Gold MD-2 pineapples grown in the field in Costa Rica were used to establish shoot cultures. Briefly, leaves of the crowns were removed by hand and discarded, the core or the stem of the crown (~3×5 cm) was washed in water, surface sterilized with 33% Clorox plus 0.05% Tween20 with stirring for 20 minutes and rinsed twice in sterile water. The lateral meristems and crown tip meristem were excised from the core by removing primary leaves one by one, while flaming the tools frequently. The crown tip meristem explant including the meristem dome, 2-3 tiny primary leaves, and 1 cm$^3$ of the stem core was placed on the shoot culture medium B2N2+CC and after 9 days to B2N2+N and after another 8 days to liquid B3 medium. Additional details relating to culture media are provided below. The lateral meristems were also isolated along with 1 cm$^3$ of the stem core and cultured on the same media as above. Cultures were incubated under continuous light at 28° C. After 20 days from initial culture, crown tip leaves had grown long, these were removed to promote the growth of crown tip meristem and were transferred to fresh B2N2 medium. After a total of 4 months from culture initiation, shoot clusters were transferred and maintained in liquid B1.5N.5 medium with monthly subculture.

2. Pretreatment of Explants for Cocultivation with *Agrobacterium*.

Rapidly growing shoots were used as explants. Tips of the long leaves (>15 mm) were cut off to provide smaller explants. Shoots were cut longitudinally into 4 sections, then leaf bases, core sections and longitudinal sections were pretreated (cultured) on P10T2.2A for 30 days then additional leaf bases and core sections were prepared and cultured on same medium until morphogenic tissues were produced. The tissues were subcultured on P10 medium for 5 weeks, then mixed with *Agrobacterium* for cocultivation.

3. *Agrobacterium tumefaciens* Culture and Preparation.

*Agrobacterium tumefaciens* strain C58pmp90 containing a vector system containing a binary vector system was used for transformation. The vector system included vector pDM containing surB gene, which confers chlorsulfuron resistance, and the gus gene encoding beta-glucuronidase. Bacteria were taken out of frozen glycerol, cultured and maintained on L-Broth medium solidified with 1.5% Bactoagar containing 10 mg/l tetracycline. One day before cocultivation, bacteria were scraped off the solid medium using a loop and suspended inn liquid MinAsuc medium and cultured for one day on a shaker (120 rpm) at 28° C. Bacteria concentration was determined, using a spectrophotometer (Beckman DU-50) before cocultivation, and was shown to be 8×10$^8$ cells/ml.

4. Cocultivation on Cocultivation Medium.

Bacteria were mixed at the volume ratio of 3:1 (plant tissue: *Agrobacterium* cells) with 80 leaf bases and core sections, tissues were blotted dry and the mixture was placed on 7.0 cm sterile Fisherbrand G6 glass filter circles on the top of cocultivation medium P10As100. Plates were parafilmed and placed in a 24° C. controlled environment incubator in the dark for 3 days.

5. Recovery, Selection and Plant Regeneration.

After cocultivation, tissues were transferred (~20 pieces/plate) to recovery medium P10Vanc100 for a recovery period of 11 days under low light condition (16 hrs/day). The explants then were transferred to selection medium P10Carb300CS10 for 25 days, P10Carb300CS20 for 28 days, T1.1I.1Carb250CS20 for 28 days, B3N.2Carb200CS10 for 28 days, B3N.2Cef400CS10 for 28 days. Carbenicillin or cefotaxime was used to kill off the residual *Agrobacterium* and chlorsulfuron (CS) to select for transformed cells. On selection medium, most of the tissues turned brown within 3-6 weeks, however occasionally some sectors of the tissues remained healthy and started growing to produce green healthy organogenic tissue. Transgenic shoots were subcultured onto B3N.2Carb100CS10 for 30 days to produce multiple shoots and shoot buds. Some of the shoots were vitrified, which then were transferred to B1A1% Carb100CS10 for 14 days to produce elongated normal shoots.

6. Confirmation of Transformation.

Shoots were confirmed to be transformed by different means: 1. CS resistant shoots or shoot primordia remained healthy and green on lethal levels of CS, 2. CS resistant shoots or shoot primordia were sampled (2-5 mg/resistant piece) for GUS assay. Transformed tissues stained blue and nontransformed tissues did not stain blue. Tissues can also be tested molecularly for transformation using PCR and, e.g., Southern blotting analyses.

7. Micropropagation and Production of Transgenic Plants.

Individual or small shoot clusters were transferred to 15 ml liquid medium B1Carb100CS20 in GA-7 cubes (2-3 clusters/cube) for propagation and growth. Optionally, 30 days later, shoot clusters can be micropropagated and maintained in B1.5N.5CS20 (containing no counterselective agents) for several months. The individual shoots (4-6 cm long) were separated and cultured in liquid rooting medium N.5IBA.5CS10 or N.5IBA.5CS20 (containing no counterselective agents) for 2-4 weeks to produce complete plants. Plants are transplanted in soil, hardened off gradually and then transferred to the greenhouse conditions.

Example 2

Transformation and Regeneration of Pineapple Del Monte Gold MD-2 Using *Agrobacterium tumefaciens* Strain C58PMP90/PDM 1. Preparation of Source Tissues (Transgenic Line 16.5.4)
   i. Establishment of Shoot Cultures.

Meristems isolated from crowns of Del Monte Gold MD-2 pineapples grown in the field in Costa Rica were used to establish shoot cultures. Briefly, leaves of the crowns were removed by hand and discarded, the core or the stem of the crown (~3×5 cm) was washed in water, surface sterilized with 33% Clorox plus 0.05% Tween20 with stirring for 25 minutes and rinsed twice in sterile water. The lateral meristems and crown tip meristem were excised from the core by removing primary leaves one by one, while flaming the tools frequently. The crown tip meristem explant including the meristem dome, 2-3 tiny primary leaves, and 1 cm$^3$ of the stem core was placed on the shoot culture medium B2N2. The lateral meristems were also isolated along with 1 cm$^3$ of the stem core and cultured on the same medium. Cultures were incubated under continuous light at 28° C. Nine days after culture initiation, the tissues were subcultured onto B2N2. After 20 days, crown tip leaves had grown long, these were removed to promote the growth of crown tip meristem and were transferred to fresh B2N2 medium. After two additional weeks, buds were formed (2-3 per explant) and subsequently new small shoots were produced to form a cluster of shoots. After a total of 4 months from culture initiation, shoot clusters were transferred and maintained in liquid B1.5N.5 medium with monthly subculture.

2. Pretreatment of Explants for Cocultivation with *Agrobacterium*.

Rapidly growing shoots were used as explants. Tips of the long leaves (>15 mm) were cut off to provide smaller explants. Shoots were cut longitudinally into 4-6 sections and pretreated (cultured) on P10T1.1b6 (containing 6% banana pulp) and P2B.5 for 8 days. Leaf bases and core sections were prepared and were mixed with *Agrobacterium* for cocultivation.

3. *Agrobacterium tumefaciens* Culture and Preparation.

*Agrobacterium tumefaciens* strain C58 pmp90 containing the binary vector system, referred to above, was used for transformation. More specifically, the vector system included vector pDM containing a surB gene and a gus gene. Bacteria were taken out of frozen glycerol, cultured and maintained on L-Broth medium solidified with 1.5% Bactoagar containing 10 mg/l tetracycline. One day before cocultivation, bacteria were scraped off the solid medium using a loop and suspended in liquid MinAsuc medium and cultured for one day on a shaker (120 rpm) at 28° C. Bacteria concentration was determined, using a spectrophotometer (Beckman DU-50) before cocultivation, and was shown to be 4.4×10$^8$ cells/ml.

4. Cocultivation on Cocultivation Medium.

Bacteria were mixed at the volume ratio of 4:1 (plant tissue: *Agrobacterium* cell) with 24 leaf bases and core sections, tissues were blotted dry and the mixture was placed on 7.0 cm sterile Fisherbrand G6 glass filter circles on the top of cocultivation medium P10T2.2As300. Plates were parafilmed and placed in a 24° C. controlled environment incubator in the dark for 3 days.

5. Recovery and Selection.

After cocultivation, tissues were transferred (15-20 pieces/plate) to recovery medium P10T1.1Carb500 for a recovery period of 7 days under low light condition (16 hrs/day). The explants then were transferred to selection medium P10T2.2Carb300CS5 for 27 days. Carbenicillin was used to kill off the residual *Agrobacterium* and chlorsulfuron (CS) to select for transformed cells. On selection medium, most of the tissues turned brown within 3-6 weeks, however occasionally some sectors of the tissues remained healthy and started growing to produce green healthy morphogenic tissue.

6. Confirmation of Putative Transformed Shoots.
   Same as Example 1.

7. Micropropagation and Production of Transgenic Plants.
   Same as Example 1.

Example 3

Transformation and Regeneration of Pineapple Del Monte Gold MD-2 Using *Agrobacterium tumefaciens* Strain C58PMP90/PDM (Transgenic Line 16.1.5, 16.1.6, and 16.1.7)

1. Preparation of Source Tissues
   i. Establishment of Shoot Cultures.
   Same as Example 2.

2. Pretreatment of Explants for Cocultivation with *Agrobacterium*.

Rapidly growing shoots were used as explants. Tips of the long leaves (>15 mm) were cut off to provide smaller explants. Shoots were cut longitudinally into 3-7 sections and pretreated (cultured) on B3N.2 medium for 12 days to produce organogenic cells and tissues, then maintained on B3N.2 medium with subculturing schedule of 28 and 31 days, then cut into 2-4 mm sections and pretreated on B3N.2 medium for 7 days. The sections were mixed with *Agrobacterium* for cocultivation.

3. *Agrobacterium tumefaciens* Culture and Preparation.

*Agrobacterium tumefaciens* strain C58 pmp90 containing the binary vector system, referred to above, was used for transformation. The vector system included vector pDM containing a surB gene and a gus gene. Bacteria were taken out of frozen glycerol, cultured and maintained on L-Broth medium solidified with 1.5% Bactoagar containing 10 mg/l tetracycline. One day before cocultivation, bacteria were scraped off the solid medium using a loop and suspended in liquid MinAsuc medium and cultured for one day on a shaker (120 rpm) at 28° C. Bacteria concentration was determined, using a spectrophotometer (Beckman DU-50) before cocultivation, and was shown to be 2, 5 and 10×10$^8$ cells/ml.

4. Cocultivation on Cocultivation Medium.

Bacteria were mixed at the volume ratio of 4:1 (plant tissue: *Agrobacterium* cell) with 24 leaf bases and core sections, tissues were blotted dry and the mixture was placed on 7.0 cm sterile Fisherbrand G6 glass filter circles on the top of cocultivation medium B3N.2As300 or B3N.2As1000. Plates were parafilmed and placed in a 24° C. controlled environment incubator in the dark for 3 days.

5. Recovery and Selection.

After cocultivation, tissues were transferred (~15 pieces/plate) to recovery medium B3N.2Carb500 for a recovery period of 6 or 7 days under low light condition (16 hrs/day). The explants then were transferred to selection medium B3N.2Carb300CS5 for 27 days. Carbenicillin was used to kill off the residual *Agrobacterium* and chlorsulfuron (CS) to select for transformed cells. On selection medium, most of the tissues turned brown within 3-6 weeks, however, occasionally some sectors of the tissues remained healthy and started growing to produce green healthy morphogenic tissue.
6. Confirmation of Putative Transformed Shoots.
   Same as Example 1.
7. Micropropagation and Production of Transgenic Plants.
   Same as Example 1.

Example 4

Transformation and Regeneration of Pineapple Del Monte Gold MD-2 Using *Agrobacterium tumefaciens* Strain C58PMP90/PDM (Transgenic Line 15.56)

1. Preparation of Source Tissues
   i. Establishment of Shoot Cultures.
   Same as Example 1.
2. Pretreatment of Explants for Cocultivation with *Agrobacterium*.
   Rapidly growing shoots were used as explants. Tips of the long leaves (>15 mm) were cut off to provide smaller explants. Shoots were cut longitudinally into 3-7 sections and pretreated (cultured) on Dic2.5B.5 medium for 8 days, then leaf bases and longitudinal sections were prepared and mixed with *Agrobacterium* for cocultivation.
3. *Agrobacterium tumefaciens* Culture and Preparation.
   *Agrobacterium tumefaciens* strain C58 pmp90 containing the binary vector system, referred to above, was used for transformation. As mentioned, the vector system included vector pDM containing a surB gene and a gus gene. Bacteria were taken out of frozen glycerol, cultured and maintained on L-Broth medium solidified with 1.5% Bactoagar containing 10 mg/l tetracycline. One day before cocultivation, bacteria were scraped off the solid medium using a loop and suspended in liquid MinAsuc medium and cultured for one day on a shaker (120 rpm) at 28° C. Bacteria concentration was determined, using a spectrophotometer (Beckman DU-50) before cocultivation, and was shown to be $3 \times 10^8$ cells/ml.
4. Cocultivation on Cocultivation Medium.
   Bacteria were mixed at the volume ratio of 3:1 (plant tissue: *Agrobacterium* cell) with 24 leaf bases and core sections, tissues were blotted dry and the mixture was placed on 7.0 cm sterile Fisherbrand G6 glass filter circles on the top of cocultivation medium Dic2.5B.5As300. Plates were parafilmed and placed in a 24° C. controlled environment incubator in the dark for 3 days.
5. Recovery and Selection.
   After cocultivation, tissues were transferred (~15 pieces/plate) to recovery medium Dic2.5B.5Carb500 for a recovery period of 10 days under low light condition (16 hrs/day). The explants then were transferred to selection medium Dic2.5B.5Carb500CS5 for 31 days with monthly subculture thereafter. Carbenicillin was used to kill off the residual *Agrobacterium* and chlorsulfuron (CS) to select for transformed cells. On selection medium, most of the tissues turned brown within 3-6 weeks, however, occasionally some sectors of the tissues remained healthy and started growing to produce green healthy morphogenic tissue.
6. Confirmation of Putative Transformed Shoots.
   Same as Example 1.
7. Micropropagation and Production of Transgenic Plants.
   Same as Example 1.

Example 5

Transformation and Regeneration of Pineapple Del Monte Gold MD-2 USING *Agrobacterium tumefaciens* Strain C58PMP90/PDM (Transgenic Line 2.77.1.1)

1. Preparation of Source Tissues
   i. Establishment of Shoot Cultures.
   Similar to Example 1 with some changes. Meristems were isolated from crowns of Del Monte Gold MD-2 pineapples grown in the field in Hawaii were used to establish shoot cultures. Briefly, leaves of the crowns were removed by hand and discarded, the core or the stem of the crown (~3×5 cm) was washed in water containing liquid soap, surface sterilized with 70% ethanol for 1 minute, 25% Clorox plus 0.05% Tween20 with stirring for 25 minutes and rinsed twice in sterile water. The lateral meristems and crown tip meristem were excised from the core by removing primary leaves one by one, while flaming the tools frequently. The crown tip meristem explant including the meristem dome, 2-3 tiny primary leaves, and 1 cm³ of the stem core was placed on the shoot culture medium B2N2. After 8 days the buds had grown and the explants were divided into smaller pieces and transferred to fresh B2N2 medium, and 10 days later to B3 medium. After additional 5 weeks the shoots were cultured in liquid B1.5N.5 medium with monthly subculture.
2. Pretreatment of Explants for Cocultivation with *Agrobacterium*.
   No pretreatment was performed in this example. Rapidly growing shoots were used as explants. Tips of the long leaves (>15 mm) were cut off to provide smaller explants. Leaf bases and core sections were prepared and without pretreatment were mixed with *Agrobacterium* for cocultivation.
3. *Agrobacterium tumefaciens* Culture and Preparation.
   Same as Example 1. Bacteria concentration was shown to be $6 \times 10^8$ cells/ml.
4. Cocultivation on Cocultivation Medium.
   Bacteria were mixed at the volume ratio of 3:1 (plant tissue: *Agrobacterium* cell) with 80 leaf bases and core sections, tissues were blotted dry and the mixture was placed on 7.0 cm sterile Fisherbrand G6 glass filter circles on the top of cocultivation medium P10T2.2AAs300. Plates were parafilmed and placed in a 24° C. controlled environment incubator in the dark for 3 days.
5. Recovery and Selection.
   After cocultivation, tissues were transferred (15-18 pieces/plate) to recovery medium P10T2.2Carb300 for a recovery period of 8 days under low light condition (16 hrs/day). The explants then were transferred to selection medium P10T2.2Carb250CS10 for 21 days P10T2.2Carb200CS10 for 28 days, P10T2.2Carb300CS5 for 20 days, P10T2.2Carb300CS5 for 30 days, B3N.2Carb100CS10 for 25 days. Carbenicillin was used to kill off the residual *Agrobacterium* and chlorsulfuron (CS) to select for transformed cells. On selection medium, most of the tissues turned brown within 3-4 weeks, however, occasionally some sectors of the tissues remained healthy and started growing to produce green healthy organogenic tissue. The organogenic tissues produced shoot on B3N.2 and B1 media series
6. Confirmation of Putative Transformed Shoots.
   Same as Example 1.
7. Micropropagation and Production of Transgenic Plants.
   Same as Example 1.

Example 6

Transformation and Regeneration of Pineapple Del Monte Gold MD-2 Using *Agrobacterium tumefaciens* strain C58PMP90/PDM (Transgenic Line 13.12.1, 13.12.2, 13.12.4)

1. Preparation of Source Tissues
   i. Establishment of Shoot Cultures.
   Similar to Example 5.
2. Preparation of Explants for Cocultivation with *Agrobacterium*.

No pretreatment was performed in this example. Rapidly growing shoots were used as explants. Tips of the long leaves (>15 mm) were cut off to provide smaller explants. Leaf bases and core sections were prepared and without pretreatment were mixed with *Agrobacterium* for cocultivation.

3. *Agrobacterium tumefaciens* Culture and Preparation.
   Same as Example 1. Two bacteria samples were used and the concentrations were shown to be $7 \times 10^8$ cells/ml and $9 \times 10^8$ cells/ml.
4. Cocultivation on Cocultivation Medium.

Bacteria were mixed at the volume ratio of 3:1 (plant tissue: *Agrobacterium* cell) with ~50 leaf bases and core sections for each treatment, the mixtures were vacuum infiltrated, then the tissues were blotted dry (13.12.1) or not (13.12.2 and 13.12.4) and the mixture was placed on 7.0 cm sterile Fisherbrand G6 glass filter circles on the top of cocultivation medium P10T2.2AAs300. Plates were parafilmed and placed in a 24° C. controlled environment incubator in the dark for 3 days.

5. Recovery and Selection.

After cocultivation, tissues were transferred (15-18 pieces/plate) to recovery medium P10T2.2ACarb300 for a recovery period of 6 days under low light condition (16 hrs/day). The explants with morphogenic potentials were transferred to selection medium P10T2.2Carb300CS5 for 21-24 days for three rounds of selection, then on B3N.2Carb100Cs10 for selection and shoot production. On selection medium, most of the tissues turned brown within 2-3 weeks, however, some sectors of the tissues remained healthy and started growing to produce green healthy organogenic tissue. The organogenic tissues produced shoot on B3N.2 and B1 media series.

6. Confirmation of Putative Transformed Shoots.
   Same as Example 1.
7. Micropropagation and Production of Transgenic Plants.
   Same as Example 1.

Media Compositions

| Minimal Asuc = MinAsuc | | |
|---|---|---|
| | preferred | range |
| potassium phosphate dibasic | 10.5 g/l | 5-20 g/l |
| potassium phosphate monobasic | 4.5 g/l | 2-8 g/l |
| ammonium sulfate | 1.0 g/l | 0.5-3 g/l |
| sodium citrate dihydrate | 0.5 g/l | 0-2 g/l |
| magnesium sulfate heptahydrate | 247 mg/l | 0-1000 g/l |
| glucose | 2.0 g/l | 1-30 g/l |

MinAsuc
MinA but with sucrose instead of glucose.
L-Broth:

| | |
|---|---|
| Tryptone | 10 g/l |
| Yeast Extract | 5 g/l |
| NaCl | 5 g/l |
| Glucose | 1 g/l |
| pH | 7.0-7.2 |
| Bacto Agar | 15 g/l |

For tissue culture media, the pH should be between about 5-7.5, preferably about 5.6. The medium is used following sterilization by autoclaving, except for specific components that are filter-sterilized and then added after autoclaving.

| | |
|---|---|
| MS | |
| MS salts | 1X |
| B5 vitamins | 1X |
| Sucrose | 30 g/l |
| MES | 600 mg/l |
| Gel-rite ® | 2.5 g/l |
| pH | 5.7 |
| B2N2 | |
| MS medium + BA | 2 mg/l |
| NAA | 2 mg/l |
| B2N2 + CC | |
| B2N2 + Carbenicillin | 500 mg/l |
| Cefotaxime | 500 mg/l |
| B2N2 + N | |
| B2N2 + Nystatin | 40 mg/l |
| B1.5N.5 LIQUID | |
| MS without Gel-rite + BA | 1.5 mg/l |
| NAA | 0.5 mg/l |
| B1CS10 | |
| MS + BA | 1 mg/l |
| Chlorsulfuron | 10 μg/l |
| B1CARB100CS10 | |
| B1CS10 + Carbenicillin | 100 mg/l |
| B3 (LIQUID) | |
| MS without Gel-rite + BA | 3 mg/l |
| B3N.2 | |
| MS + BA | 3 mg/l |
| NAA | 0.2 mg/l |
| B3N.2AS300 | |
| B3N.2 + Acetosyringone | 300 μM |
| B3N.2AS1000 | |
| B3N.2 + Acetosyringone | 1000 μM |
| B3N.2CARB500 | |
| B3N.2 + Carbenicillin | 500 mg/l |
| B3N.2CARB100CS10 | |
| B3N.2 + Carbenicillin | 100 mg/l |
| Chlorsulfuron | 10 μg/l |
| B3N.2CARB300CS5 | |
| B3N.2 + Carbenicillin | 300 mg/l |
| Chlorsulfuron | 5 μg/l |
| B3N.2CARB200CS10 | |
| B3N.2 + Carbenicillin | 200 mg/l |
| Chlorsulfuron | 10 μg/l |

| | |
|---|---|
| B3N.2CEF400CS10 | |
| B3N.2 + Cefotaxime | 400 mg/l |
| Chlorsulfuron | 10 µg/l |
| B3N.2CS20 | |
| B3N.2 + Chlorsulfuron | 20 µg/l |
| B1 | |
| MS + BA | 1 mg/l |
| B1A1% | |
| B1 + Agar | 10 g/l |
| (instead of Gel-rite) | |
| B1 LIQUID | |
| B1 without Gel-rite | |
| B3 | |
| MS + BA | 3 mg/l |
| DIC2.5B.5 | |
| MS + Dicamba | 2.5 mg/l |
| BA | 0.5 mg/l |
| DIC2.5B.5AS300 | |
| Dic2.5B.5 + Acetosyringone | 300 µM |
| DIC2.5B.5CARB500 | |
| Dic2.5B.5 + Carbenicillin | 500 mg/l |
| DIC2.5B.5CARB500CS5 | |
| Dic2.5B.5Carb500 + Chlorsulfuron | 5 µg/l |
| P2B.5 | |
| MS + Picloram | 2 mg/l |
| BA | 0.5 mg/l |
| P10 | |
| MS + Picloram | 10 mg/l |
| P10AS100 | |
| P10 + Acetosyringone | 100 µM |
| P10CARB300CS10 | |
| P10 + Carbenicillin | 300 mg/l |
| Chlorsulfuron | 10 µg/l |
| P10CARB300CS20 | |
| P10Carb300 + Chlorsulfuron | 20 µg/l |
| P10T1.1B6 | |
| MS + Picloram | 10 mg/l |
| Thidiazuron | 1.1 mg/l |
| Banana Pulp | 6% |
| P10T1.1CARB500 | |
| MS + Picloram | 10 mg/l |
| Thidiazuron | 1.1 mg/l |
| Carbenicillin | 500 mg/l |
| P10T2.2 | |
| MS + Picloram | 10 mg/l |
| Thidiazuron | 2.2 mg/l |
| P10T2.2A | |
| P10T2.2 + agar instead of gel-rite | |
| P10T2.2AAS300 | |
| P10T2.2A + Acetosyringone | 300 µM |
| P10T2.2ACARB 300 | |
| P10T2.2A + Carbenicillin | 300 mg/l |
| P10T2.2AS300 | |
| P10T2.2 + Acetosyringone | 300 µM |
| P10T2.2CARB200CS10 | |
| P10T2.2 + Carbenicillin | 200 mg/l |
| Chlorsulfuron | 10 µg/l |
| P10T2.2CARB250CS10 | |
| P10T2.2 + Carbenicillin | 250 mg/l |
| Chlorsulfuron | 10 µg/l |
| P10T2.2CARB300 | |
| P10T2.2 + Carbenicillin | 300 mg/l |
| P10T2.2CARB300CS5 | |
| P10T2.2Carb300 + Chlorsulfuron | 5 µg/l |
| P10B.5 | |
| MS + Picloram | 10 mg/l |
| BA | 0.5 mg/l |
| P10VANC100 | |
| MS + Picloram | 10 mg/l |
| Vanc | 100 mg/l |
| N.5I.5 LIQUID | |
| MS without Gel-rite + NAA | 0.5 mg/l |
| IBA | 0.5 mg/l |
| T1.1I.1CARB250CS20 | |
| MS + Thidiazuron | 1.1 mg/l |
| IBA | 0.1 mg/l |
| Carbenicillin | 250 mg/l |
| Chlorsulfuron | 20 µg/l |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of generating a plant comprising transformed plant cells, the method comprising:
   culturing at least one non-apical meristemic cell to produce at least one shoot;
   culturing at least one leaf base explant from the shoot to produce one or more organogenic cells;
   introducing at least one nucleic acid segment into the organogenic cells to produce one or more transformed organogenic cells, wherein the nucleic acid segment is introduced into the organogenic cells using *Agrobacterium*-mediated delivery; and
   generating at least one plant from the transformed organogenic cells without going through an undifferentiated intermediate.

2. The method of claim 1, wherein the non-apical meristemic cell comprises a pineapple cell.

3. The method of claim 1,
   wherein the nucleic acid segment comprises at least one sense nucleic acid segment that corresponds to at least a portion of at least one endogenous gene;
   wherein the nucleic acid segment comprises at least one sense nucleic acid segment that corresponds to at least a portion of at least one exogenous gene;
   wherein the nucleic acid segment comprises at least one antisense nucleic acid segment that corresponds to at least a portion of at least one endogenous gene;

wherein the nucleic acid segment encodes at least one polypeptide transcription factor; or, wherein the nucleic acid segment encodes at least one promoter and/or at least one enhancer, which nucleic acid segment homologously recombines with at least one promoter and/or at least one enhancer of at least one endogenous gene.

4. The method of claim 1, wherein the nucleic acid segment encodes a polypeptide.

5. The method of claim 4, wherein the polypeptide is heterologous to the organogenic cells.

6. The method of claim 4, wherein the polypeptide is homologous to at least one endogenous polypeptide of the organogenic cells.

7. The method of claim 4, wherein the polypeptide comprises at least one carotenoid biosynthetic polypeptide that is selected from the group consisting of: an isomerase, an isopentenyl diphosphate isomerase, a geranylgeranyl pyrophosphate synthase, a phytoene synthase, a phytoene desaturase, a ζ-carotene desaturase, a lycopene β-cyclase, a lycopene ε-cyclase, a β-carotene hydroxylase, and an ε-hydroxylase.

* * * * *